(12) United States Patent
Yang et al.

(10) Patent No.: US 9,771,334 B2
(45) Date of Patent: Sep. 26, 2017

(54) TRIKETONE COMPOUND AND PREPARATION METHOD AND USE THEREOF

(71) Applicants: SHANDONG CYNDA CHEMICAL CO., LTD.; WEIFANG CYNDA CHEMICAL CO., LTD., Weifang (CN)

(72) Inventors: Guangfu Yang, Wuhan (CN); Dawei Wang, Wuhan (CN); Qiong Chen, Wuhan (CN)

(73) Assignees: SHANDONG CYNDA CHEMICAL CO., LTD., Boxing County, Shandong (CN); WEIFANG CYNDA CHEMICAL CO., LTD., Weifang, Shandong (CN)

( * ) Notice: Subject to any disclaimer, the term of this patent is extended or adjusted under 35 U.S.C. 154(b) by 0 days.

(21) Appl. No.: 15/031,956

(22) PCT Filed: May 21, 2014

(86) PCT No.: PCT/CN2014/078005
§ 371 (c)(1),
(2) Date: Apr. 25, 2016

(87) PCT Pub. No.: WO2015/058519
PCT Pub. Date: Apr. 30, 2015

(65) Prior Publication Data
US 2016/0264532 A1 Sep. 15, 2016

(30) Foreign Application Priority Data

Oct. 25, 2013 (CN) .......................... 2013 1 0516269

(51) Int. Cl.
*C07D 239/96* (2006.01)
*A01N 43/54* (2006.01)
*C07D 239/95* (2006.01)

(52) U.S. Cl.
CPC ........... *C07D 239/96* (2013.01); *A01N 43/54* (2013.01); *C07D 239/95* (2013.01)

(58) Field of Classification Search
CPC ..... C07D 239/96; C07D 239/95; A01N 43/54
See application file for complete search history.

(56) References Cited

U.S. PATENT DOCUMENTS

| | | | |
|---|---|---|---|
| 2008/0004180 | A1 | 1/2008 | Dollinger et al. |
| 2010/0222341 | A1 | 9/2010 | Schiemann et al. |
| 2010/0222592 | A1 | 9/2010 | Takabe et al. |
| 2011/0287937 | A1 | 11/2011 | Takabe et al. |

FOREIGN PATENT DOCUMENTS

| | | | |
|---|---|---|---|
| CN | 101808988 A | 8/2010 | |
| CN | 102246790 A | 11/2011 | |
| EP | 1188376 A1 * | 3/2002 | ............ A01N 43/18 |
| WO | 2007/088876 A1 | 8/2007 | |
| WO | 2010/089993 A1 | 8/2010 | |
| WO | 2012/033548 A1 | 3/2012 | |

OTHER PUBLICATIONS

Nie et al., "Recent advances in triketone herbicide research," Chinese Journal of Pesticides, vol. 45, No. 1, Jan. 2006, 5 pages (English Abstract included).

* cited by examiner

*Primary Examiner* — John Pak
*Assistant Examiner* — Andriae M Holt
(74) *Attorney, Agent, or Firm* — Volpe and Koenig, P.C.

(57) ABSTRACT

Disclosed in the present invention is a triketone compound which has a structure shown in Formula (I). Also disclosed in the present invention is a method for preparing the triketone compound having a structure as shown by Formula (I), which comprise that under the rearrangement reaction conditions, the compound having a structure as shown by Formula (II) is contacted with a catalyst in the presence of a base and a solvent. Further disclosed in the present invention is the use of a triketone compound having a structure as shown by Formula (I) in preventing and controlling weeds. Said triketone compound having a structure as shown by formula (I) in the present invention has the effect of preventing and controlling weeds, in particular having an excellent effect on preventing and controlling broadleaved weeds and/or gramineae weeds.

20 Claims, 1 Drawing Sheet

TRIKETONE COMPOUND AND PREPARATION METHOD AND USE THEREOF

CROSS REFERENCE TO RELATED APPLICATIONS

This application is a 35 USC §371 national stage application of PCT/CN2014/078005, which was filed May 5, 2014 and claims priority to Chinese Patent Application No. 201310516269.0, filed Oct. 25, 2013, both of which are incorporated herein by reference as if fully set forth.

FIELD OF THE INVENTION

The present invention relates to a triketone compound as well as its preparation method and its use for preventing and controlling weeds.

BACKGROUND OF THE INVENTION 4-hydroxyphenylpyruvate dioxygenase (4-HPPD) is a new action target of herbicides discovered in the 1980s and widely exists in various aerobic organisms. This enzyme is a dioxygenase containing iron divalent and relying on α-ketonic acid. It can catalytically convert p-hydroxyphenylpyruvic acid into homogentisic acid. The action mechanism of 4-HPPD herbicide is a process of inhibiting conversion of p-hydroxyphenylpyruvic acid inside plants into homogentisic acid. The homogentisic acid inside plants can be further biologically catalyzed into plastoquinone and tocopherol, while plastoquinone and tocopherol are substances necessary for transfer of electron chain in plant photosynthesis. If 4-HPPD in plants is inhibited, the synthesis of homogentisic acid will be obstructed, thus affecting the transfer of electron chain of photosynthesis in plants. Consequently, the plants will suffer whitening and die.

Designing and synthesizing 4-HPPD inhibitor with a new structure is one of the hotspot fields for pesticide chemical research in the recent years. By now, 4-HPPD inhibitors with more than five different structures have been discovered and mainly include triketone type, pyrazole type, isoxazole type, diketone nitrile type and benzophenone type. The herbicides developed with 4-HPPD as a target have a string of advantages, such as: high performance, low toxicity, environmental friendliness, and safety to subsequent crops. Therefore, 4-HPPD herbicides have a great research value and development prospect and also attract more and more pesticide companies to the R&D of 4-HPPD herbicides. On the market, there are many kinds of triketone-type 4-HPPD inhibitors. Their molecules all have a benzene ring structure, such as: mesotrione and sulcotrione. Among them, mesotrione has the best herbicidal effect and high safety.

Based on the research on 4-HPPD herbicide system, the present invention designs and synthesizes a new triketone-type 4-HPPD compound containing quinazolinedione structure.

SUMMARY OF THE INVENTION

The object of the present invention is to provide a new triketone compound containing quinazolinedione structure and its preparation method and its use for preventing and controlling weeds.

In order to realize the above object, on the one hand, the present invention provides a triketone compound, which has a structure shown in Formula (I):

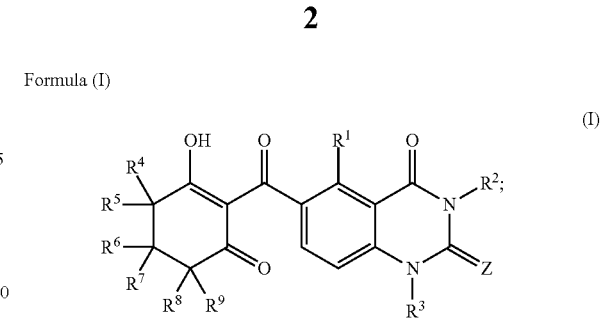

Formula (I)

wherein, Z is O or S; $R^1$ is one of H, $C_1$-$C_6$ alkyl, halogen, nitro, $C_1$-$C_6$ alkoxy and cyano; $R^2$ is one of substituted or unsubstituted phenyl, benzyl, diaromatic group and triaromatic group; $R^3$ is one of H, $C_1$-$C_6$ alkyl, $C_2$-$C_6$ unsaturated chain alkyl, substituted or unsubstituted phenyl, and substituted or unsubstituted benzyl; $R^4$, $R^5$, $R^6$, $R^7$, $R^8$ and $R^9$ are respectively one of H, $C_1$-$C_6$ alkyl, $C_1$-$C_6$ alkoxy and halogen.

On the second hand, the present invention provides a method for preparing the triketone compound with a structure shown in Formula (I). This method includes contacting the compound with a structure shown in Formula (II) with catalyst under the conditions of rearrangement reaction with the existence of alkali and solvent;

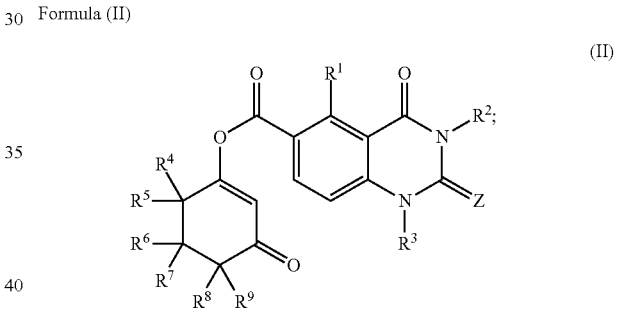

Formula (II)

wherein, Z is O or S; $R^1$ is one of H, $C_1$-$C_6$ alkyl, halogen, nitro, $C_1$-$C_6$ alkoxy and cyano; $R^2$ is one of substituted or unsubstituted phenyl, benzyl, diaromatic group and triaromatic group; $R^3$ is one of H, $C_1$-$C_6$ alkyl, $C_2$-$C_6$ unsaturated chain alkyl, substituted or unsubstituted phenyl, and substituted or unsubstituted benzyl; $R^4$, $R^5$, $R^6$, $R^7$, $R^8$ and $R^9$ are respectively one of H, $C_1$-$C_6$ alkyl, $C_1$-$C_6$ alkoxy and halogen.

On the third hand, the present invention provides use of the triketone compound with a structure shown in Formula (I) for preventing and controlling weeds.

The triketone compound provided by the present invention, having a structure shown in Formula (I) and containing quinazolinedione structure has an effect in preventing and controlling weeds, particularly broadleaved weeds and/or gramineae weeds.

Other features and advantages of the present invention will be elaborated in the subsequent embodiments.

BRIEF DESCRIPTION OF THE DRAWINGS

The accompanying drawings are intended to provide further understanding on the present invention and constitute a part of the description. They and the embodiments below together are intended to explain the present invention and not to limit the present invention. Of the accompanying drawings.

DETAILED DESCRIPTION OF THE EMBODIMENTS

Figure 1:
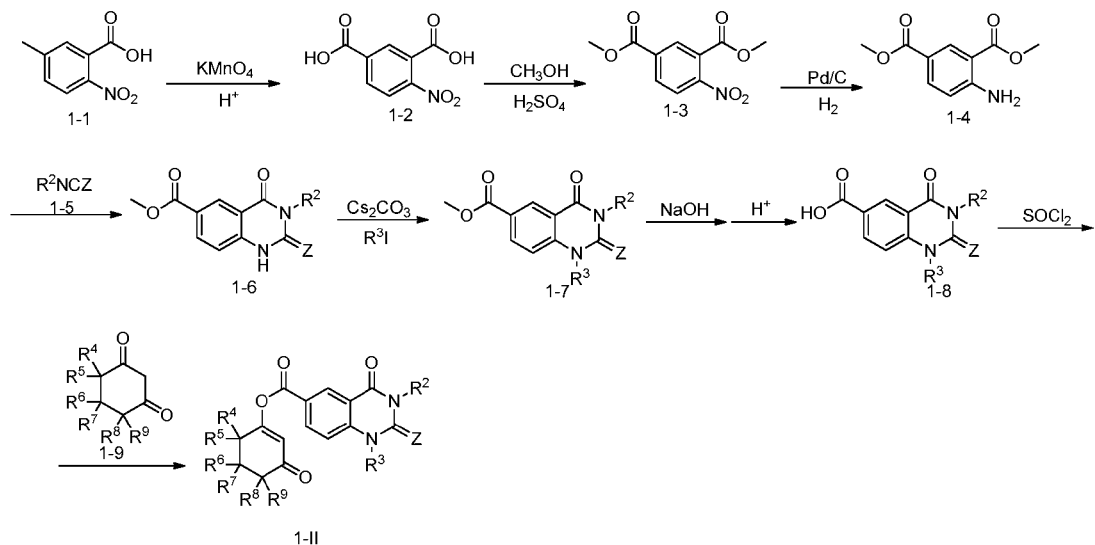
FIG. 1 shows a synthetic route for synthesis of the compound with a structure shown in Formula (II) when $R^1$ is H.

Thereafter the embodiments of the present invention will be described in details. It should be understood that these embodiments are intended to describe and explain the present invention and not to limit the present invention.

On the one hand, the present invention provides a triketone compound, which has a structure shown in Formula (I):

Formula (I)

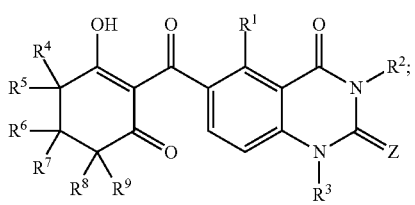

wherein,

Z may be O or S; $R^1$ may be one of H, $C_1$-$C_6$ alkyl, halogen, nitro, $C_1$-$C_6$ alkoxy and cyano; $R^2$ may be one of substituted or unsubstituted phenyl, benzyl, diaromatic group and triaromatic group; $R^3$ may be one of H, $C_1$-$C_6$ alkyl, $C_2$-$C_6$ unsaturated chain alkyl, substituted or unsubstituted phenyl, and substituted or unsubstituted benzyl; $R^4$, $R^5$, $R^6$, $R^7$, $R^8$ and $R^9$ may be respectively one of H, $C_1$-$C_6$ alkyl and $C_1$-$C_6$ alkoxy and halogen.

According to the triketone compound with a structure shown in Formula (I) described in the present invention, when Z is O or S; $R^1$ is one of H, $C_1$-$C_6$ alkyl, halogen, nitro, $C_1$-$C_6$ alkoxy and cyano; $R^2$ is one of substituted or unsubstituted phenyl, benzyl, diaromatic group and triaromatic group; $R^3$ is one of H, $C_1$-$C_6$ alkyl, $C_2$-$C_6$ unsaturated chain alkyl, substituted or unsubstituted phenyl, and substituted or unsubstituted benzyl; $R^4$, $R^5$, $R^6$, $R^7$, $R^8$ and $R^9$ is respectively one of H, $C_1$-$C_6$ alkyl, $C_1$-$C_6$ alkoxy and halogen, this triketone compound will have an effect in preventing and controlling weeds.

The substitutent groups of $R^2$ and $R^3$ may be respectively halogen, $C_1$-$C_6$ alkyl, $C_1$-$C_6$ alkoxy, $C_1$-$C_6$ halogenated alkyl, nitro and $C_1$-$C_6$ halogenated alkoxy for example. The $C_1$-$C_6$ alkyl may be methyl, ethyl, propyl, isobutyl, n-butyl, tertiary butyl, 2,2-dimethyl propyl, amyl and hexyl for example. The $C_1$-$C_6$ alkoxy may be methoxy, ethyoxy, propoxy, isopropoxy, n-butoxy, tert-butoxy, 2,2-methylpropoxy, amoxy and hexyloxy for example. The halogen may be F, Cl, Br and I for example.

Preferably, Z is O; $R^1$ is one of H and $C_1$-$C_3$ alkyl; $R^2$ is one of substituted or unsubstituted phenyl and substituted or unsubstituted diaromatic group; $R^3$ is one of H, $C_1$-$C_6$ alkyl, $C_2$-$C_4$ unsaturated chain alkyl, substituted or unsubstituted phenyl, and substituted or unsubstituted benzyl; $R^4$, $R^5$, $R^6$, $R^7$, $R^8$ and $R^9$ are respectively one of H and $C_1$-$C_6$ alkyl. The present invention particularly prefers the triketone compound with a structure shown in Formula (I), wherein $R^1$ is H or methyl; $R^4$, $R^5$, $R^6$, $R^7$, $R^8$ and $R^9$ are respectively H or methyl.

Preferably $R^2$ and $R^3$ are respectively methyl, halogen-substituted phenyl, methyl-substituted phenyl, trifluoromethyl-substituted phenyl, methoxy-substituted phenyl, trifluoromethoxy-substituted phenyl, isopropyl-substituted phenyl, ethyl-substituted phenyl, and naphthyl and nitro-substituted phenyl.

More preferably, the triketone compound is a compound shown in Table 1.

Under the forgoing preferred circumstances, the effect of the triketone compound with a structure shown in Formula (I) in preventing and controlling weeds may be further enhanced.

On the second hand, the present invention provides a method for preparing a triketone compound with a structure shown in Formula (I). This method includes contacting the compound with a structure shown in Formula (II) with catalyst under the conditions of rearrangement reaction with the existence of alkali and solvent;

Formula (I)

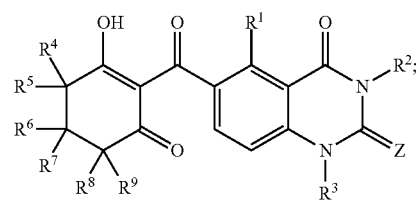

Formula (II)

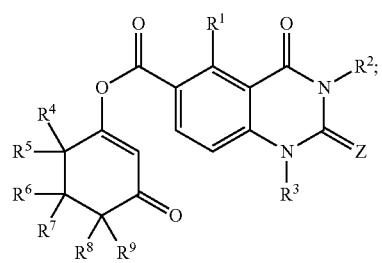

wherein, the substitutent groups in the structures shown in Formula (I) and Formula (II) may be as described in the preceding part of the present invention.

According to the method for preparing a triketone compound with a structure shown in Formula (I) as described in the present invention, those skilled in the art may have the compound with a structure shown in Formula (II) contact with catalyst in accordance with the normal conditions and operation of rearrangement reaction and with the existence of alkali and solvent. Preferably, the contact conditions are: reaction temperature 0-100° C., more preferably 20-40° C.; reaction time 0.5-24 h, more preferably 5-12 h.

In the preparation method described in the present invention, the molar ratio of the compound with a structure shown in Formula (II) to catalyst and alkali is preferably 1:0.01-1:0.5-4, more preferably 1:0.05-1:1-3.

Those skilled in the art should understand that the method described in the present invention may also include a step of purifying the obtained product. There are no particular requirements for purifying method. The purifying methods conventionally used by those skilled in the art may be adopted. For example, impurities may be removed by such methods as extraction by extracting agent, drying by drying agent and column chromatography.

In the preparation method described in the present invention, the compound with a structure shown in Formula (II) may be bought from the market or prepared through conventional reactions in the art.

For example, when in the compound with a structure shown in Formula (II), Z is O or S; $R^1$ is H; $R^2$ is one of substituted or unsubstituted phenyl, benzyl, diaromatic group and triaromatic group; $R^3$ is one of H, $C_1$-$C_6$ alkyl, $C_2$-$C_6$ unsaturated chain alkyl, substituted or unsubstituted phenyl, and substituted or unsubstituted benzyl; $R^4$, $R^5$, $R^6$, $R^7$, $R^8$ and $R^9$ are respectively one of H, $C_1$-$C_6$ alkyl, $C_1$-$C_6$ alkoxy and halogen, the compound with a structure shown in Formula (II) may be prepared by the synthetic route as shown in FIG. 1: under an acidic condition and with the existence of $KMnO_4$, 1-1 compound is oxidized to obtain 1-2 compound; the obtained compound reacts with methanol with the existence of $H_2SO_4$ to obtain 1-3 compound; the obtained compound takes reduction reaction with hydrogen with the existence of Pd/C catalyst to obtain 1-4 compound; 1-4 compound reacts with 1-5 compound to obtain 1-6 compound; 1-6 compound reacts with alkyl iodine with the existence of cesium carbonate to obtain 1-7 compound; it takes further reactions under a basic condition and an acidic condition in turn to obtain 1-8 compound; 1-8 compound reacts with sulfoxide chloride and 1-9 compound in turn to obtain the compound with a structure shown in Formula (II).

When in the compound with a structure shown in Formula (II), Z is O or S; $R^1$ is one of $C_1$-$C_6$ alkyl, halogen, nitro, $C_1$-$C_6$ alkoxy and cyano; $R^2$ is one of substituted or unsubstituted phenyl, benzyl, diaromatic group and triaromatic group; $R^3$ is one of H, $C_1$-$C_6$ alkyl, $C_2$-$C_6$ unsaturated chain alkyl, substituted or unsubstituted phenyl, and substituted or unsubstituted benzyl; $R^4$, $R^5$, $R^6$, $R^7$, $R^8$ and $R^9$ are respectively one of H, $C_1$-$C_6$ alkyl, $C_1$-$C_6$ alkoxy and halogen, the compound with a structure shown in Formula (II) may be prepared by the synthetic route as shown in FIG. 2: 2-1 compound reacts with ICl to obtain 2-2 compound; it further reacts with 2-3 compound to obtain 2-4 compound; 2-4 compound reacts with alkyl iodine with the existence of cesium carbonate to obtain 2-5 compound; it further reacts with cuprous cyanide to obtain 2-6 compound, and then takes acidification reaction to obtain 2-7 compound; 2-7 compound reacts with sulfoxide chloride and 2-8 compound in turn to obtain the compound with a structure shown in Formula (II).

Figure 2:
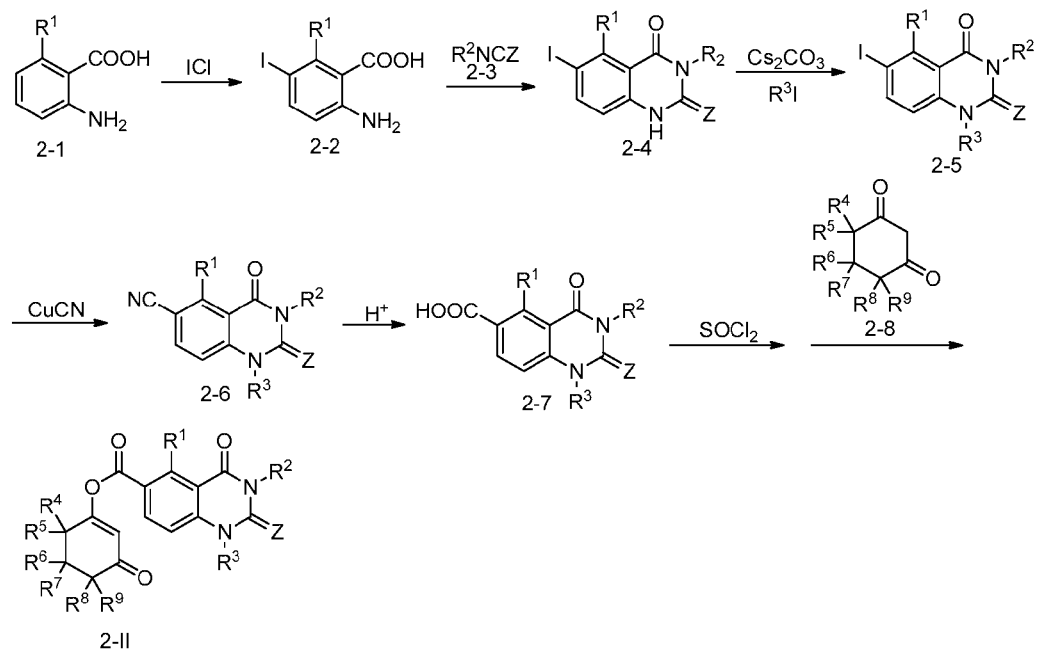
FIG. 2 shows a synthetic route for synthesis of the compound with a structure shown in Formula (II) when $R^1$ is one of $C_1$-$C_6$ alkyl, halogen, nitro, $C_1$-$C_6$ alkoxy and cyano.

The substituent groups of the compounds in the synthetic route as shown in FIG. 1 and FIG. 2 in the present invention have the foregoing types.

In the preparation method described in the present invention, the catalyst is preferably at least one of sodium cyanide, potassium cyanide, acetone cyanohydrins, trimethyl silyl cyanide, 1,2,4-triazole and benzo-1,2,4-triazole; the alkali is preferably at least one of potassium carbonate, sodium carbonate, cesium carbonate, triethylamine and pyridine; the solvent is preferably at least one of dichloromethane, trichloromethane, dichloroethane, acetonitrile, toluene, tetrahydrofuran and benzene.

On the third hand, the present invention provides use of the foregoing triketone compound for preventing and controlling weeds.

The weeds described in the present invention refer to the plants which live in human living and activity sites and do harm to human living and activities. They may be wild plants or plants useless to human. For example, they may be wild plants in crop planting fields.

Preferably, the foregoing triketone compound provided by the present invention has a good effect when it is used to prevent and control broadleaved weeds and/or gramineae weeds.

Preferably, the weeds may be one or more of *abutilon theophrasti, digitaria sanguinalis, amaranthus retroflexus, echinochloa crusgalli, eclipta prostrata* and *setaria viridis*.

In the use of the foregoing triketone compound provided by the present invention, the preferred dose of the triketone compound is 50-300 g/ha.

In the use of the foregoing triketone compound provided by the present invention, the triketone compound is dissolved in and diluted with a solvent before use. The preferred concentration after the dissolution and dilution is 0.05-0.4 g/L. The solvents dissolving the triketone compound may include N,N-dimethylformamide, dimethylsulfoxide, etc. The reagent used for dilution may be water which contains common additives. Preferably, additives commonly used in herbicides in the art may be added to the solution containing dissolved triketone compound, for example: one or a plurality of surface agents and emulsifying agents.

The diluted triketone compound described in the present invention may be sprayed onto stems and/or leaves of plants by a conventional method of the art.

In order to enhance the prevention and control effect of the triketone compound described in the present invention and extend its use scope, the triketone compound may be used separately, or together with other common herbicides (such as: atrazine, fentrazamide, bromoxynil, and pentoxazone) in a compound way. Moreover, there isn't particular limitation to compounding ratio, and a ratio normally used in the art may be adopted as long as the prevention and control effect is enhanced, the use scope is extended and safety performance is improved after compounding.

Below the present invention is described in details by referring to examples. Unless otherwise stated in the following examples, the raw materials used in the examples are purchased from the market and are all analytically pure.

Preparation Example 1

This preparation example is for preparing (3-oxo-1-cyclohexenyl)-3-(4-chlorphenyl)-1-methyl-2,4-dioxo-1,2,3,4-tetrahydroquinazolinedione-6-carboxylate, and includes the following steps:

Step A: Preparation of 4-nitroisophthalic Acid

Add 20 g of 5-methyl-2-nitrobenzoic acid to a 500 mL single-neck flask, install a reflux condensing tube, add 200 mL of water, add 2 g of KOH under agitation, heat to 90° C., add 50 g of $KMnO_4$ by batch after the solid in the reaction flask is thoroughly dissolved, and continue to react at 90° C. for 3-4 h. Perform suction filtration while it is hot after the reaction, and wash the filter cakes with hot water. Acidify the filtrate with concentrated HCl in an ice-water bath, adjust pH value to 1-2 and let it rest to separate out a large amount of solid. Perform suction filtration, wash the solid with water and dry it to obtain a white solid. The output is 21.6 g and the yield is 92.7%; mp 244-246° C. $^1$H NMR (600 MHz, DMSO-D$_6$): δ 13.99 (brs, 2H), 8.34 (d, J=1.2 Hz, 1H), 8.27 (dd, J=8.4, 1.8 Hz, 1H), 8.08 (d, J=8.4 Hz, 1H).

Step B: Preparation of dimethyl 4-nitroisophthalate

Add 31 g of 4-nitroisophthalic acid to a 500 mL single-neck flask, add 200 mL of methanol, slowly dropwise add 4 mL of concentrated H$_2$SO$_4$, perform reflux after the dropwise addition, react overnight, dry off methanol after the reaction, add 100 mL of water, extract with 100 mL×2 of ethyl acetate twice, wash the organic layer with 30 mL of saturated NaHCO$_3$ twice, dry with anhydrous Na$_2$SO$_4$, and dry off the solvent to obtain a white crystalline pure product. The output is 28.4 g and the yield is 95%; mp 84-86° C. $^1$H (600 MHz, CDCl$_3$): δ 8.44 (s, 1H), 8.29 (d, J=8.4 Hz, 1H), 7.93 (d, J=8.4 Hz, 1H), 7.27 (s, 1H), 3.99 (s, 3H), 3.95 (s, 3H).

Step C: Preparation of dimethyl 4-aminoisophthalate

Dissolve 20 g of dimethyl 4-nitroisophthalate in 518 mL of ethyl acetate and add 1 g of 10 wt % of Pd/C under agitation. Input H$_2$, slowly heat to 40° C., react for about 5 h, and track the reaction process by TLC until the raw materials disappear. Stop heating after the reaction, cool the product to room temperature and filter it, wash filter cakes with ethyl acetate, and carry out column chromatography, eluent:petroleum ether:ethyl acetate=3:1. 17 g of white crystalline solid is obtained and the yield is 97%; mp 127-129° C. $^1$H (400 MHz, CDCl$_3$): δ 8.59 (d, J=1.6 Hz, 1H), 7.91 (dd, J=8.4 Hz, 2.0 Hz, 1H), 6.66 (d, J=8.8 Hz, 1H), 6.2 (brs, 2H), 3.90 (s, 3H), 3.88 (s, 3H).

Step D: Preparation of methyl-3-(4-chlorphenyl)-2, 4-dioxo-1,2,3,4-tetrahydroquinazolinedione-6-carboxylate Add 2 g of dimethyl 4-aminoisophthalate to a 50 mL double-neck flask, add 20 mL of pyridine and 1.86 g of p-chlorophenyl isocyanate and react at 100° C. overnight. Add 30 mL of water after the reaction, separate out a large amount of white precipitate, perform suction filtration, wash the solid with diethyl ether and dry it to obtain 2.99 g of white solid, with a yield of 95%; mp 311-313° C. $^1$H NMR (600 MHz, DMSO-D$_6$): δ 11.95 (s, 1H), 8.48 (d, J=1.8 Hz, 1H), 8.23 (dd, J=9.0, 1.8 Hz, 1H), 7.56 (d, J=8.4 Hz, 2H), 7.40 (d, J=8.4 Hz, 2H), 7.32 (d, J=8.4 Hz, 1H), 3.88 (s, 3H).

Step E: Preparation of methyl-3-(-4-chlorphenyl)-1-methyl-2,4-dioxo-1,2,3,4-tetrahydroquinazolinedione-6-carboxylate Add 3 g of methyl-3-(4-chlorphenyl)-2,4-dioxo-1,2,3,4-tetrahydroquinazolinedione-6-carboxylate to a 150 mL single-neck flask, add 50 mL of DMF and 3 g of Cs$_2$CO$_3$ and react under agitation for 30 min. Dropwise add 5 g of CH$_3$I, and react at room temperature overnight after the dropwise addition. Add 100 mL of water after the reaction, separate out a large amount of white precipitate, perform suction filtration, wash the precipitate with water and dry it to obtain 2.82 g of white solid, with a yield of 91%; mp 232-234° C. $^1$H NMR (600 MHz, DMSO-D$_6$): δ 8.57 (s, 1H), 8.33 (d, J=8.4 Hz, 1H), 7.65 (d, J=9.0 Hz, 1H), 7.58 (d, J=8.4 Hz, 2H), 7.39 (d, J=7.8 Hz, 2H), 3.90 (s, 3H), 3.57 (s, 3H).

Step F: Preparation of 3-(-4-chlorphenyl)-1-methyl-2,4-dioxo-1,2,3,4-tetrahydroquinazolinedione-6-carboxylic acid Add 3 g of methyl-3-(-4-chlorphenyl)-1-methyl-2,4-dioxo-1,2,3,4-tetrahydroquinazolinedione-6-carboxylate to a 250 mL double-neck flask, add 70 mL of ethanol, dropwise add a solution prepared by dissolving 0.68 g of NaOH in 70 mL of water, slowly raise temperature to 45° C. after the dropwise addition, take reaction for 3 h, and track the reaction process by TLC. Dropwise add concentrated HCl in an ice bath after the reaction to adjust pH value to 1-2, separate out a large amount of white precipitate, filter it and dry it to obtain 1.6 g of white solid, with a yield of 56%; mp 314-316° C. $^1$H NMR (400 MHz, DMSO-D$_6$): δ 13.22 (brs, 1H), 8.57 (s, 1H), 8.30 (d, J=8.4 Hz, 1H), 7.62 (d, J=9.2 Hz, 1H), 7.57 (d, J=8.0 Hz, 2H), 7.39 (d, J=8.0 Hz, 2H), 3.57 (s, 3H).

Step G: Preparation of (3-oxo-1-cyclohexenyl)-3-(-4-chlorphenyl)-1-methyl-2,4-dioxo-1,2,3,4-tetrahydroquinazolinedione-6-carboxylate Add 1 g of 3-(4-chlorphenyl)-1-methyl-2,4-dioxo-1,2,3, 4-tetrahydroquinazolinedione-6-carboxylic acid to a 50 mL single-neck flask, add 10 mL of THF, slowly dropwise add 1 g of SOCl$_2$, heat to 75° C. after the dropwise addition, react under reflux for 2 h, track the reaction process by TLC, and dry off the solvent after the reaction. Add 20 mL of dry CHCl$_3$, 0.41 g of 1,3-cyclohexanedione, and 0.4 g of Et$_3$N, react under agitation for about 0.5 h, and track the reaction process by TLC. Wash with 20 mL of water once, with 10 mL of 1 mol/L HCl twice and 10 mL of saturated NaHCO$_3$ twice after the reaction, dry with anhydrous Na$_2$SO$_4$, and pass the column, with eluent being petroleum ether:acetone=5:1. 0.79 g of white solid is obtained, with a yield of 62%; mp 179-181° C. $^1$H NMR (600 MHz, CDCl$_3$): δ 8.93 (s, 1H), 8.41 (d, J=8.4 Hz, 1H), 7.51 (d, J=8.4 Hz, 2H), 7.39 (d, J=9.0 Hz, 1H), 7.22 (d, J=8.4 Hz, 2H), 6.08 (s, 1H), 3.70 (s, 3H), 2.70 (t, J=6.0 Hz, 2H), 2.48 (t, J=6.0 Hz, 2H), 2.14 (quintuplet, J=6.6 Hz, 2H).

Preparation Example 2

This preparation example is for preparing (3-oxo-1-cyclohexenyl)-3-(4-chlorphenyl)-1-methyl-2,4-dioxo-1,2,3,4-tetrahydroquinazolinedione-6-carboxylate, and includes the following steps:

Step A: Preparation of methyl-4-O-2-S-3-(o-tolyl)-1,2,3,4-tetrahydroquinazolinedione-6-carboxylate Add 6.7 g of dimethyl 4-aminoisophthalate to a 100 mL double-neck flask, add 30 mL of pyridine and 6 g of o-methylphenylthioisocyanate and react at 100° C. overnight. Add 40 mL of water after the reaction, stir for 30 min, separate out a large amount of white solid, perform suction filtration and wash the solid with diethyl ether. Dry the solid to obtain a pure product. The output is 9.45 g and the yield is 90%; mp 227-229° C. $^1$H NMR (600 MHz, DMSO-D$_6$): δ 13.38 (s, 1H), 8.47 (s, 1H), 8.30 (d, J=9.0 Hz, 1H), 7.53 (d, J=9.0 Hz, 1H), 7.36-7.28 (m, 3H), 7.23 (d, J=7.2 Hz, 1H), 3.89 (s, 3H), 2.06 (s, 3H).

Step B: Preparation of methyl-1-methyl-4-O-2-S-3-(o-tolyl)-1,2,3,4-tetrahydroquinazolinedione-6-carboxylate Add 7 g of methyl-4-O-2-S-3-(o-tolyl)-1,2,3,4-tetrahydroquinazolinedione-6-carboxylate to a 250 mL single-neck flask, add 90 mL of DMF and 8.4 g of $Cs_2CO_3$, and react at room temperature under agitation for about 30 min Dropwise add 10 g of $CH_3I$, and react at room temperature under agitation overnight. Add 100 mL of water after the reaction, separate out a large amount of white precipitate, perform suction filtration, wash the solid with water, and dry it to obtain 6.21 g of white solid, with a yield of 85%; mp 160-162° C. $^1$H NMR (600 MHz, DMSO-$D_6$): δ 8.64 (s, 1H), 8.33 (d, J=8.4 Hz, 1H), 7.74 (d, J=8.4 Hz, 1H), 7.52-7.45 (m, 2H), 7.44-7.38 (m, 2H), 3.91 (s, 3H), 2.53 (s, 4H), 2.07 (s, 3H).

Step C: Preparation of 1-methyl-4-O-2-S-3-(o-tolyl)-1,2,3,4-tetrahydroquinazolinedione-6-carboxylic acid Add 6.5 g of methyl-1-methyl-4-O-2-S-3-(o-tolyl)-1,2,3,4-tetrahydroquinazolinedione-6-carboxylate to a 250 mL reaction flask, add 80 mL of methanol, dropwise add a solution consisting of 2 g of $LiOH \cdot H_2O$ and 80 mL of water, slowly raise temperature to 45° C. after the dropwise addition, react for 3 h and track the reaction process by TLC. Remove THF and methanol under reduced pressure after the reaction. Extract the obtained liquid with ethyl acetate twice, 20 mL each time. Neutralize the water layer in an ice bath with concentrated HCl till pH value is 1-2. Let it rest and separate out a large amount of white solid, filter the solid, wash the obtained precipitate with diethyl ether and dry it to obtain 3 g of white solid, with a yield of 48%; mp 266-268° C. $^1$H NMR (400 MHz, DMSO-$D_6$): δ 13.22 (brs, 1H), 8.57 (s, 1H), 8.30 (d, J=8.4 Hz, 1H), 7.62 (d, J=9.2 Hz, 1H), 7.57 (d, J=8.0 Hz, 2H), 7.39 (d, J=8.0 Hz, 2H), 3.57 (s, 3H).

Step D

Preparation of 5,5-dimethyl-(3-oxo-1-cyclohexenyl)-1-methyl-4-O-2-S-3-(o-tolyl)-1,2,3,4-tetrahydroquinazoline-6-carboxylate Add 0.9 g of 1-methyl-4-O-2-S-3-(o-tolyl)-1,2,3,4-tetrahydroquinazolinedione-6-carboxylic acid to a 100 mL single-neck flask, add 18 mL of dry THF, slowly dropwise add 1.8 g of $SOCl_2$ at room temperature, react under reflux at 75° C. for about 3 h after the dropwise addition, and dry off the solvent after the reaction.

Add 50 mL of dry $CHCl_3$, 0.43 g of 5,5-dimethyl-1,3-cyclohexanedione, and 0.5 g of $Et_3N$, react for about 0.5 h and track the reaction process by TLC. Wash with 20 mL of water once, with 1 mol/l HCl twice, 10 mL each time and with saturated $NaHCO_3$ twice, 10 mL each time after the reaction, dry with anhydrous $Na_2SO_4$, pass the column, with eluent being petroleum ether:acetone=4:1. 1 g of white solid is obtained, with a yield of 80%; mp 128-130° C. $^1$H NMR (600 MHz, $CDCl_3$): δ 8.97 (s, 1H), 8.38 (d, J=8.4 Hz, 1H), 7.73 (d, J=8.4 Hz, 1H), 7.48 (t, J=7.8 Hz, 1H), 7.42 (d, J=7.8 Hz, 1H), 7.39 (t, J=7.8 Hz, 1H), 7.22 (d, J=7.8 Hz, 1H), 6.09 (s, 1H), 2.58 (s, 2H), 2.57 (s, 3H), 2.34 (s, 2H), 2.17 (s, 3H), 1.17 (s, 6H).

Preparation Example 3

This preparation example is for preparing (3-oxo-1-cyclohexenyl)-3-(4-chlorphenyl)-1-methyl-2,4-dioxo-1,2,3,4-tetrahydroquinazolinedione-6-carboxylate, and includes the following steps:

Step A: Preparation of 6-amino-3-iodine-2-dimethylbenzoic acid

Add 3 g of 2-amino-6-methyl benzoic acid to a 100 mL reaction flask at room temperature, add 30 mL of glacial acetic acid (dose 1 mmol=2 mL) under agitation, dissolve 4 g of ICl in 10 mL of glacial acetic acid, dropwise add the solution into the foregoing reaction system under agitation within 15 min, and continue to react under agitation for about 2.5 h after the dropwise addition. Filter the reaction solution under reduced pressure after the reaction, wash the obtained solid with 10 mL of acetonitrile and 10 mL of glacial acetic acid respectively, and dry it to obtain 4.07 g of off-white solid, with a yield of 74%; melting point: 186-188° C. $^1$H NMR (600 MHz, DMSO-$D_6$): δ 8.97 (brs, 3H), 7.72 (d, J=8.4 Hz, 1H), 6.75 (d, J=7.8 Hz, 1H), 2.40 (s, 3H).

Step B: Preparation of 6-iodine-5-methyl-3-(2-(trifluoromethyl)phenyl)quinazoline-2,4(1H,3H)-dione Add 5 g of 6-amino-3-iodine-2-dimethylbenzoic acid to a 100 mL double-neck flask, add 36 mL of pyridine, and slowly add 4.22 g of o-trifluoromethylphenylisocyanate to the system under agitation. Heat the reaction solution to 100° C., react overnight, remove pyridine through reduced pressure distillation after the reaction, dissolve the obtained solid in acetone, and pass the column (the eluent is petroleum:acetone=6:1) to obtain 6 g of white solid, with a yield of 75%; melting point: 195-197° C. $^1$H NMR (600 MHz, DMSO-$D_6$): δ 11.72 (s, 1H), 8.14 (d, J=9.0 Hz, 1H), 7.88 (d, J=7.8 Hz, 1H), 7.84 (t, J=7.8 Hz, 1H), 7.70 (t, J=7.8 Hz, 1H), 7.62 (d, J=7.8 Hz, 1H), 6.94 (d, J=8.4 Hz, 1H), 2.80 (s, 3H).

Step C: Preparation of 6-iodine-1,5-dimethyl-3-(2-(trifluoromethyl)phenyl)quinazoline-2,4(1H,3H)-dione Add 5 g of 6-iodine-5-methyl-3-(2-(trifluoromethyl)phenyl)quinazoline-2,4(1H,3H)-dione to a 200 mL single-neck flask, add 50 mL of DMF, add 5 g of $Cs_2CO_3$ under agitation, continue the agitation and react for about 30 min. Slowly dropwise add 6 g of $CH_3I$ to the reaction system, and react under agitation at room temperature overnight after the dropwise addition. Add 100 mL of water to the system after the reaction, and extract the reaction system with ethyl acetate 3 times, 50 mL each time. Merge the organic layer, dry it with anhydrous sodium sulfate, and pass the column (petroleum:acetone=10:3) to obtain 4.7 g of white product, with a yield of 91%; melting point: 195-197° C. $^1$H NMR (600 MHz, $CDCl_3$): δ 8.15 (d, J=9.0 Hz, 1H), 7.83 (d, J=7.8 Hz, 1H), 7.73 (t, J=7.8 Hz, 1H), J=7.8 Hz, 1H), 7.35 (d, J=7.8 Hz, 1H), 6.93 (d, J=9.0 Hz, 1H), 3.61 (s, 3H), 2.96 (s, 3H).

Step D

Preparation of 1,5-dimethyl-2,4-dioxo-3-(2-(trifluoromethyl)phenyl)-1,2,3,4-tetrahydroquinazoline-6-cyano Add 7 g of 6-iodine-1,5-dimethyl-3-(2-(trifluoromethyl)phenyl)quinazoline-2,4(1H,3H)-dione, and 8 g of CuCN to a 200 mL double-neck flask and add 60 mL of dry DMF. React under reflux for 12 h, remove DMF through reduced pressure distillation after the reaction, add 60 mL of acetone to the reaction flask after cooling, stir violently for 20 min, and remove unreacted CuCN by filtration. Pass the filtrate through the column (eluent:petroleum:acetone=10:3) to obtain 4.5 g of white solid, with a yield of 82%, melting point: 224-226° C. $^1$H NMR (600 MHz, CDCl3): δ 7.91 (d, J=8.4 Hz, 1H), 7.85 (d, J=7.8 Hz, 1H), 7.75 (t, J=7.8 Hz, 1H), 7.63 (t, J=7.8 Hz, 1H), 7.35 (d, J=7.2 Hz, 1H), 7.27 (d, J=8.4 Hz, 1H), 3.67 (s, 3H), 2.97 (s, 3H).

Step E: Preparation of 1,5-dimethyl-2,4-dioxo-3-(2-(trifluoromethyl)phenyl)-1,2,3,4-tetrahydroquinazoline-6-carboxylic acid Add 4.5 g of 1,5-dimethyl-2,4-dioxo-3-(2-(trifluoromethyl)phenyl)-1,2,3,4-tetrahydroquinazoline-6-cyano to a 250 mL reaction flask, and add 50 mL of glacial acetic acid, 50 mL of water and 50 mL of concentrated $H_2SO_4$ under agitation. Raise temperature to 120° C., react for 12 h, cool to room temperature after the reaction, pour the reaction system to a beaker containing 200 mL of icy water, add 100 mL of ethyl acetate to the beaker to extract the organic layer, extract the water layer with 100 mL of ethyl acetate twice, merge organic layer after extraction, further extract the organic layer with 50% NaOH solution 3 times, 30 mL each time, merge the water layer, acidify the water layer with concentrated HCl till pH value is 1-2, let it rest to separate out a large amount of white solid, and perform suction filtration to obtain 1.8 g of pure product, with a yield of 38%; melting point: 296-298° C. $^1$H NMR (600 MHz, DMSO-D$_6$): δ 13.23 (s, 1H), 8.07 (d, J=9.0 Hz, 1H), 7.89 (d, J=7.8 Hz, 1H), 7.85 (t, J=7.8 Hz, 1H), 7.71 (t, J=7.8 Hz, 1H), 7.63 (d, J=7.8 Hz, 1H), 7.47 (d, J=9.0 Hz, 1H), 3.56 (s, 3H), 2.82 (s, 3H).

Step F: Preparation of (3-oxo-1-cyclohexenyl)-1,5-dimethyl-2,4-dioxo-3-(2-(trifluoromethyl)-phenyl)-1,2,3,4-tetrahydroquinazoline-6-carboxylate Add 1 g of 1,5-dimethyl-2,4-dioxo-3-(2-(trifluoromethyl)phenyl)-1,2,3,4-tetrahydroquinazoline-6-carboxylic acid to a 50 mL single-neck flask, add 18 mL of dry THF, slowly dropwise add 1.8 g of $SOCl_2$ at room temperature, react under reflux at 75° C. for about 1.5 h after the dropwise addition, track the reaction process by TLC, and dry off the solvent after the reaction. Add 20 mL of dry $CHCl_3$, 0.41 g of 1,3-cyclohexanedione, 0.43 g of $Et_3N$, react for about 0.5 h, and track the reaction by TLC until acyl chloride disappears. Wash with 20 mL of water once, with 1 mol/L of HCl twice, 10 mL each time and with saturated $NaHCO_3$ twice, 10 mL each time after the reaction, dry it with anhydrous $Na_2SO_4$, and pass the column, with eluent being petroleum: acetone=4:1. The output is 0.79 g, and the yield is 62%; mp 157-159° C. $^1$H NMR (600 MHz, CDCl$_3$): δ 8.18 (d, J=8.4 Hz, 1H), 7.85 (d, J=7.8 Hz, 1H), 7.75 (t, J=7.8 Hz, 1H), 7.63 (t, J=7.8 Hz, 1H), 7.37 (d, J=7.8 Hz, 1H), 7.25 (d, J=8.4 Hz, 1H), 6.05 (s, 1H), 3.68 (s, 3H), 3.00 (s, 3H), 2.70 (t, J=6.0 Hz, 2H), 2.49 (t, J=6.0 Hz, 2H), 2.15 (quintuplet, J=6.0 Hz, 2H).

Example 1

This example prepares 3-(4-chlorphenyl)-6-[(2-hydroxy-6-oxo-1-cyclohexenyl)carbonyl]-1-methylquinazoline-2,4(1H,3H)-dione according to the synthetic route as shown in FIG. 1.

Add 0.7 g of (3-oxo-1-cyclohexenyl)-3-(4-chlorphenyl)-1-methyl-2,4-dioxo-1,2,3,4-tetrahydroquinazolinedione-6-carboxylate obtained in preparation example 1 of the present invention to a 50 mL double-neck flask, add 28 mL of anhydrous acetonitrile, add 0.58 g of $Et_3N$ and 0.014 g (10% equivalent) of acetone cyanohydrin under the protection of $N_2$. React at room temperature for 20 h, and track the reaction by TLC until the raw materials disappear. Dry off acetonitrile after the reaction, and add about 38 mL of $CHCl_3$. Wash with 1 mol/L HCl 3 times, 10 mL each time and with saturated sodium chloride 3 times, 10 mL each time, and dry the organic layer with anhydrous sodium sulfate. Remove the solvent under reduced pressure to obtain light yellow oily substance, and recrystallize the oily substance with 10 mL of methanol to obtain 0.53 g of light yellow solid, with a yield of 75%; mp 234-236° C. $^1$H NMR (600 MHz, CDCl$_3$): δ 16.77 (s, 1H), 8.39 (d, J=1.8 Hz, 1H), 7.90 (dd, J=8.4, 1.8 Hz, 1H), 7.48 (d, J=8.4 Hz, 2H), 7.28 (d, J=9.0 Hz, 1H), 7.21 (d, J=8.4 Hz, 2H), 3.66 (s, 3H), 2.77 (t, J=6.6 Hz, 2H), 2.51 (t, J=6.6 Hz, 2H), 2.09 (quintuplet, J=6.6 Hz, 2H). $^{13}$C NMR (101 MHz, CDCl$_3$): δ 196.44, 196.33, 194.23, 160.98, 150.66, 142.85, 135.45, 134.58, 133.69, 133.07, 130.19, 129.71, 129.51, 114.86, 113.10, 113.01, 37.90, 32.16, 31.03, 18.90.

Example 2

This example prepares 6-[(2-hydroxy-4,4-dimethyl-6-oxo-1-cyclohexenyl)carbonyl]-1-methyl-2-thio-3-(o-tolyl)-2,3-dihydroxyquinazoline-4(1H)-ketone according to the synthetic route as shown in FIG. 1.

Add 0.85 g of 5,5-dimethyl-(3-oxo-1-cyclohexenyl)-1-methyl-4-O-2-S-3-(o-tolyl)-1,2,3,4-tetrahydroquinazoline-6-carboxylate obtained in preparation example 2 of the present invention to a 100 mL double-neck flask, add 38 mL of anhydrous dichloromethane, add 0.38 g of $Et_3N$ and 0.01 g (10% equivalent) of acetone cyanohydrin under the protection of $N_2$. React at room temperature for 10 h, and track the reaction by TLC until the raw materials disappear. Extract with 1 mol/L HCl 3 times, 10 mL each time, wash with saturated sodium chloride 3 times, 10 mL each time, and dry the organic layer with anhydrous sodium sulfate. Dry off the solvent, and recrystallize the product with 10 mL of methanol to obtain 0.65 g of light yellow solid, with a yield of 77%; mp 239-241° C. $^1$H NMR (600 MHz, CDCl$_3$): δ 16.89 (s, 1H), 8.40 (s, 1H), 7.85 (d, J=8.4 Hz, 1H), 7.64 (d, J=8.4 Hz, 1H), 7.45 (t, J=7.2 Hz, 1H), 7.38 (dd, J=19.2, 8.4 Hz, 2H), 7.20 (d, J=7.8 Hz, 1H), 2.66 (s, 2H), 2.55 (s, 3H), 2.41 (s, 2H), 2.16 (s, 3H), 1.16 (s, 6H). $^{13}$C NMR (101 MHz, CDCl$_3$): δ 196.67, 195.29, 193.96, 160.55, 160.29, 150.05, 136.75, 135.09, 134.67, 134.17, 131.32, 130.29, 129.02, 128.48, 127.27, 125.49, 118.88, 112.26, 52.02, 45.93, 30.99, 28.26, 17.37, 15.37.

Example 3

This example prepares 6-[(2-hydroxy-6-oxo-1-cyclohexenyl)carbonyl]-1,5-dimethyl-3-(2-(trifluoromethyl)phenyl) quinazoline-2,4(1H,3H)-dione according to the synthetic route as shown in FIG. 2.

Add 0.7 g of (3-oxo-1-cyclohexenyl) 1,5-dimethyl-2,4-dioxo-3-(2-(trifluoromethyl)phenyl)-1,2,3,4-tetrahydroquinazoline-6-carboxylate obtained in preparation example 3 of the present invention to a 50 mL double-neck flask, add 28 mL of anhydrous acetonitrile, and add 0.38 g of $Et_3N$, 0.018 g (10% equivalent) of acetone cyanohydrin under the protection of $N_2$. React at room temperature for 8 h, and track the reaction by TLC until the raw materials disappear. Dry off acetonitrile after the reaction and add about 30 mL of $CHCl_3$. Wash with 1 mol/L HCl 3 times, 10 mL each time and with saturated sodium chloride 3 times, 10 mL each time, and dry the organic layer with anhydrous sodium sulfate. Remove the solvent under reduced pressure to obtain light yellow oily substance, and recrystallize the oily substance with 10 mL of methanol to obtain 0.55 g of light yellow solid, with a yield of 78%; mp 262-264° C. $^1$H NMR (600 MHz, CDCl$_3$): δ 17.64 (s, 1H), 7.83 (d, J=7.2 Hz, 1H), 7.72 (t, J=7.8 Hz, 1H), 7.60 (t, J=7.2 Hz, 1H), 7.41 (d, J=8.4 Hz, 1H), 7.35 (d, J=7.8 Hz, 1H), 7.20 (d, J=8.4 Hz, 1H), 3.64 (s, 3H), 2.81 (t, J=6.0 Hz, 2H), 2.65 (s, 3H), 2.46 (t, J=6.0 Hz, 2H), 2.07 (quintuplet, J=6.0 Hz, 2H).

By the foregoing similar method, a series of compounds as shown in Table A and Table B were also synthesized. All the compounds have been confirmed by NMR and HRMS.

TABLE A

| NO. | R$^1$ | R$^2$ | R$^3$ | R$^4$ | R$^5$ | R$^6$ | R$^7$ | R$^8$ | R$^9$ | Z |
|---|---|---|---|---|---|---|---|---|---|---|
| 1 | H | 4-Cl—C$_6$H$_4$ | CH$_3$ | H | H | H | H | H | H | O |
| 2 | H | 4-Cl—C$_6$H$_4$ | CH$_3$ | H | H | CH$_3$ | CH$_3$ | H | H | O |
| 3 | H | 3-Cl—C$_6$H$_4$ | CH$_3$ | H | H | H | H | H | H | O |
| 4 | H | 3-Cl—C$_6$H$_4$ | CH$_3$ | H | H | CH$_3$ | CH$_3$ | H | H | O |
| 5 | H | 2-Cl—C$_6$H$_4$ | CH$_3$ | H | H | H | H | H | H | O |
| 6 | H | 2-Cl—C$_6$H$_4$ | CH$_3$ | H | H | CH$_3$ | CH$_3$ | H | H | O |
| 7 | H | 3,5-di-Cl—C$_6$H$_3$ | CH$_3$ | H | H | H | H | H | H | O |
| 8 | H | 3,5-di-Cl—C$_6$H$_3$ | CH$_3$ | H | H | CH$_3$ | CH$_3$ | H | H | O |
| 9 | H | 4-F—C$_6$H$_4$ | CH$_3$ | H | H | H | H | H | H | O |
| 10 | H | 3-F—C$_6$H$_4$ | CH$_3$ | H | H | H | H | H | H | O |
| 11 | H | 3-F—C$_6$H$_4$ | CH$_3$ | H | H | CH$_3$ | CH$_3$ | H | H | O |
| 12 | H | 2-F—C$_6$H$_4$ | CH$_3$ | H | H | H | H | H | H | O |
| 13 | H | 2-F—C$_6$H$_4$ | CH$_3$ | H | H | CH$_3$ | CH$_3$ | H | H | O |
| 14 | H | 4-CH$_3$—C$_6$H$_4$ | CH$_3$ | H | H | H | H | H | H | O |
| 15 | H | 4-CH$_3$—C$_6$H$_4$ | CH$_3$ | H | H | CH$_3$ | CH$_3$ | H | H | O |
| 16 | H | 4-CH$_3$—C$_6$H$_4$ | CH$_3$ | H | H | H | CH$_3$ | H | H | O |
| 17 | H | 3-CH$_3$—C$_6$H$_4$ | CH$_3$ | H | H | H | H | H | H | O |
| 18 | H | 3-CH$_3$—C$_6$H$_4$ | CH$_3$ | H | H | CH$_3$ | CH$_3$ | H | H | O |
| 19 | H | 3-CH$_3$—C$_6$H$_4$ | CH$_3$ | H | H | CH$_3$ | H | H | H | O |
| 20 | H | 2-CH$_3$—C$_6$H$_4$ | CH$_3$ | H | H | H | H | H | H | O |
| 21 | H | 2-CH$_3$—C$_6$H$_4$ | CH$_3$ | H | H | CH$_3$ | CH$_3$ | H | H | O |
| 22 | H | 4-F—C$_6$H$_4$ | CH$_3$ | H | H | CH$_3$ | CH$_3$ | H | H | O |
| 23 | H | 3-Br—C$_6$H$_4$ | CH$_3$ | H | H | H | H | H | H | O |
| 24 | H | 3-Br—C$_6$H$_4$ | CH$_3$ | H | H | CH$_3$ | CH$_3$ | H | H | O |
| 25 | H | 4-Br—C$_6$H$_4$ | CH$_3$ | H | H | H | H | H | H | O |
| 26 | H | 4-Br—C$_6$H$_4$ | CH$_3$ | H | H | CH$_3$ | CH$_3$ | H | H | O |
| 27 | H | 2-Br—C$_6$H$_4$ | CH$_3$ | H | H | H | H | H | H | O |
| 28 | H | 2-Br—C$_6$H$_4$ | CH$_3$ | H | H | CH$_3$ | CH$_3$ | H | H | O |
| 29 | H | 2-OCH$_3$—C$_6$H$_4$ | CH$_3$ | H | H | H | H | H | H | O |
| 30 | H | 4-CF$_3$—C$_6$H$_4$ | CH$_3$ | H | H | H | H | H | H | O |
| 31 | H | 4-CF$_3$—C$_6$H$_4$ | CH$_3$ | H | H | CH$_3$ | CH$_3$ | H | H | O |
| 32 | H | 2,6-di-Cl—C$_6$H$_3$ | CH$_3$ | H | H | H | H | H | H | O |
| 33 | H | 2-CH$_3$-5-Cl—C$_6$H$_3$ | CH$_3$ | H | H | H | H | H | H | O |
| 34 | H | 2,6-di-CH$_3$—C$_6$H$_3$ | CH$_3$ | H | H | H | H | H | H | O |
| 35 | H | C$_6$H$_5$ | CH$_3$ | H | H | H | H | H | H | O |
| 36 | H | 4-CH(CH$_3$)$_2$—C$_6$H$_4$ | CH$_3$ | H | H | H | H | H | H | O |
| 37 | H | 2-CH$_3$-5-Cl—C$_6$H$_3$ | CH$_3$ | H | H | CH$_3$ | CH$_3$ | H | H | O |
| 38 | H | 2-CF$_3$—C$_6$H$_4$ | CH$_3$ | H | H | H | H | H | H | O |
| 39 | H | 2-OCF$_3$—C$_6$H$_4$ | CH$_3$ | H | H | H | H | H | H | O |
| 40 | H | C$_6$H$_5$ | CH$_3$ | H | H | CH$_3$ | CH$_3$ | H | H | O |
| 41 | H | 2-CF$_3$—C$_6$H$_4$ | CH$_3$ | H | H | CH$_3$ | CH$_3$ | H | H | O |
| 42 | H | C$_6$H$_5$ | CH$_3$ | H | H | CH$_3$ | H | H | H | O |
| 43 | H | 4-Cl—C$_6$H$_4$ | CH$_2$CH$_3$ | H | H | H | H | H | H | O |
| 44 | H | 1-naphthyl | CH$_3$ | H | H | H | H | H | H | O |
| 45 | H | 4-NO$_2$—C$_6$H$_4$ | CH$_3$ | H | H | H | H | H | H | O |
| 46 | H | 2,6-di-CH(CH$_3$)$_2$—C$_6$H$_3$ | CH$_3$ | H | H | H | H | H | H | O |
| 47 | H | 2-CH$_2$CH$_3$—C$_6$H$_4$ | CH$_3$ | H | H | H | H | H | H | O |
| 48 | H | 2-OCH$_3$—C$_6$H$_4$ | CH$_3$ | H | H | CH$_3$ | CH$_3$ | H | H | O |
| 49 | H | 4-OCF$_3$—C$_6$H$_4$ | CH$_3$ | H | H | CH$_3$ | CH$_3$ | H | H | O |
| 50 | H | 4-OCF$_3$—C$_6$H$_4$ | CH$_3$ | H | H | H | H | H | H | O |
| 51 | H | 3-CF$_3$—C$_6$H$_4$ | CH$_3$ | H | H | CH$_3$ | CH$_3$ | H | H | O |
| 52 | H | 3-CF$_3$—C$_6$H$_4$ | CH$_3$ | H | H | H | H | H | H | O |
| 53 | H | 4-NO$_2$—C$_6$H$_4$ | CH$_3$ | H | H | CH$_3$ | CH$_3$ | H | H | O |
| 54 | H | 2,6-di-CH$_3$—C$_6$H$_3$ | CH$_3$ | CH$_3$ | CH$_3$ | H | H | H | H | O |
| 55 | H | 3-OCH$_3$—C$_6$H$_4$ | CH$_3$ | H | H | H | H | H | H | O |
| 56 | H | 3-OCH$_3$—C$_6$H$_4$ | CH$_3$ | H | H | CH$_3$ | CH$_3$ | H | H | O |
| 57 | H | 4-OCH$_3$—C$_6$H$_4$ | CH$_3$ | H | H | H | H | H | H | O |
| 58 | H | 4-OCH$_3$—C$_6$H$_4$ | CH$_3$ | H | H | CH$_3$ | CH$_3$ | H | H | O |
| 59 | H | 2-CH$_3$—C$_6$H$_4$ | H | H | H | CH$_3$ | CH$_3$ | H | H | O |
| 60 | H | 2-Cl-5-CF$_3$—C$_6$H$_3$ | CH$_3$ | H | H | H | H | H | H | O |
| 61 | H | 2-Cl-5-CF$_3$—C$_6$H$_3$ | CH$_3$ | H | H | CH$_3$ | CH$_3$ | H | H | O |
| 62 | H | 2,4-di-Cl—C$_6$H$_3$ | CH$_3$ | H | H | H | H | H | H | O |
| 63 | H | 2,4-di-Cl—C$_6$H$_3$ | CH$_3$ | H | H | CH$_3$ | CH$_3$ | H | H | O |
| 64 | H | 2,4-di-Cl—C$_6$H$_3$ | CH$_3$ | H | H | H | CH$_3$ | H | H | O |
| 65 | H | 2-CH(CH$_3$)$_2$—C$_6$H$_4$ | CH$_3$ | H | H | H | H | H | H | O |
| 66 | H | 2-CH$_3$—C$_6$H$_4$ | CH$_2$CH$_3$ | H | H | H | H | H | H | O |
| 67 | H | 2,4,6-tri-CH$_3$—C$_6$H$_2$ | CH$_3$ | H | H | H | H | H | H | O |
| 68 | H | 2-CH$_3$—C$_6$H$_4$ | H | H | H | H | H | H | H | O |
| 69 | H | 2-CH$_3$—C$_6$H$_4$ | CH$_2$CH$_3$ | H | H | CH$_3$ | CH$_3$ | H | H | O |
| 70 | H | 2-CH$_3$—C$_6$H$_4$ | CH$_2$CH$_3$ | H | H | H | CH$_3$ | H | H | O |

TABLE B

| NO. | R¹ | R² | R³ | R⁴ | R⁵ | R⁶ | R⁷ | R⁸ | R⁹ | Z |
|---|---|---|---|---|---|---|---|---|---|---|
| 71 | H | 2-CH$_3$—C$_6$H$_4$ | CH$_2$CH$_2$CH$_3$ | H | H | H | H | H | H | O |
| 72 | H | 2-CH$_3$—C$_6$H$_4$ | CH$_2$CH$_2$CH$_3$ | H | H | CH$_3$ | CH$_3$ | H | H | O |
| 73 | H | 2-CH$_3$—C$_6$H$_4$ | CH$_2$CH$_2$CH$_2$CH$_3$ | H | H | H | H | H | H | O |
| 74 | H | 2-CH$_3$—C$_6$H$_4$ | CH$_2$CH$_2$CH$_2$CH$_3$ | H | H | CH$_3$ | CH$_3$ | H | H | O |
| 75 | H | 2-CH$_3$—C$_6$H$_4$ | CH$_2$CH(CH$_3$)$_2$ | H | H | H | H | H | H | O |
| 76 | H | 2-CH$_3$—C$_6$H$_4$ | CH$_2$CH(CH$_3$)$_2$ | H | H | CH$_3$ | CH$_3$ | H | H | O |
| 77 | H | 2-CH$_3$—C$_6$H$_4$ | CH$_2$C≡CH | H | H | H | H | H | H | O |
| 78 | H | 2-CH$_3$—C$_6$H$_4$ | CH$_2$C≡CH | H | H | CH$_3$ | CH$_3$ | H | H | O |
| 79 | H | 2-CH$_3$—C$_6$H$_4$ | CH$_2$C$_6$H$_5$ | H | H | H | H | H | H | O |
| 80 | H | 2-CH$_3$—C$_6$H$_4$ | CH$_2$C$_6$H$_5$ | H | H | CH$_3$ | CH$_3$ | H | H | O |
| 81 | H | 2-CH$_3$—C$_6$H$_4$ | CH$_2$-3-OCH$_3$—C$_6$H$_4$ | H | H | CH$_3$ | CH$_3$ | H | H | O |
| 82 | CH$_3$ | 2-CH$_3$—C$_6$H$_4$ | CH$_3$ | H | H | H | H | H | H | O |
| 83 | H | 2-CH$_3$—C$_6$H$_4$ | CH$_2$-2-F—C$_6$H$_4$ | H | H | H | H | H | H | O |
| 84 | H | 2-CH$_3$—C$_6$H$_4$ | CH$_2$-3-OCH$_3$—C$_6$H$_4$ | H | H | H | H | H | H | O |
| 85 | H | 2-CH$_3$—C$_6$H$_4$ | CH$_2$-2-F—C$_6$H$_4$ | H | H | CH$_3$ | CH$_3$ | H | H | O |
| 86 | H | 2-CH$_3$—C$_6$H$_4$ | CH$_3$ | H | H | H | H | H | H | S |
| 87 | H | 2-CH$_3$—C$_6$H$_4$ | CH$_3$ | H | H | CH$_3$ | CH$_3$ | H | H | S |
| 88 | CH$_3$ | 2-OCH$_3$—C$_6$H$_4$ | CH$_3$ | H | H | H | H | H | H | O |
| 89 | H | 2-CH$_2$CH$_3$—C$_6$H$_4$ | CH$_3$ | H | H | CH$_3$ | CH$_3$ | H | H | O |
| 90 | H | 4-Br—C$_6$H$_4$ | CH$_3$ | H | H | CH$_3$ | H | H | H | O |
| 91 | CH$_3$ | 2-CF$_3$—C$_6$H$_4$ | CH$_3$ | H | H | CH$_3$ | CH$_3$ | H | H | O |
| 92 | CH$_3$ | 2-CF$_3$—C$_6$H$_4$ | CH$_3$ | H | H | H | H | H | H | O |
| 93 | CH$_3$ | 2,6-di-CH$_3$—C$_6$H$_3$ | CH$_3$ | H | H | H | H | H | H | O |
| 94 | H | 2,6-di-Cl—C$_6$H$_3$ | CH$_3$ | H | H | CH$_3$ | CH$_3$ | H | H | O |
| 95 | H | 2-CH$_3$-6-Cl—C$_6$H$_3$ | CH$_3$ | H | H | H | H | H | H | O |
| 96 | H | 2-CH$_3$-6-Cl—C$_6$H$_3$ | CH$_3$ | H | H | CH$_3$ | CH$_3$ | H | H | O |
| 97 | H | 2-CH(CH$_3$)$_2$C$_6$H$_4$ | CH$_3$ | H | H | H | H | H | H | O |
| 98 | H | 2,6-di-CH$_3$—C$_6$H$_3$ | CH$_3$ | H | H | CH$_3$ | CH$_3$ | H | H | O |

The physical properties and NMR characteristic data of each compound are shown in Table 1.

TABLE 1

| NO. | Appearance | Melting point/° C. | ¹HNMR |
|---|---|---|---|
| 1 | Light yellow solid | 234-236 | ¹H NMR (600 MHz, CDCl$_3$): δ 16.77 (s, 1H), 8.39 (d, J = 1.8 Hz, 1H), 7.90 (dd, J = 8.4, 1.8 Hz, 1H), 7.48 (d, J = 8.4 Hz, 2H), 7.28 (d, J = 9.0 Hz, 1H), 7.21 (d, J = 8.4 Hz, 2H), 3.66 (s, 3H), 2.77 (t, J = 6.6 Hz, 2H), 2.51 (t, J = 6.6 Hz, 2H), 2.09 (quintuplet, J = 6.6 Hz, 2H). |
| 2 | Light yellow solid | 146-148 | ¹H NMR (600 MHz, CDCl$_3$): δ 16.82 (s, 1H), 8.38 (d, J = 1.2 Hz, 1H), 7.88 (dd, J = 8.4, 1.8 Hz, 1H), 7.48 (d, J = 8.4 Hz, 2H), 7.28 (d, J = 9.0 Hz, 1H), 7.21 (d, J = 8.4 Hz, 2H), 3.66 (s, 3H), 2.66 (s, 2H), 2.40 (s, 2H), 1.15 (s, 6H). |
| 3 | Light yellow solid | 139-141 | ¹H NMR (600 MHz, CDCl$_3$): δ 16.77 (s, 1H), 8.39 (d, J = 1.8 Hz, 1H), 7.90 (dd, J = 8.4, 1.8 Hz, 1H), 7.47-7.42 (m, 2H), 7.28 (d, J = 8.4 Hz, 2H), 7.17-7.18 (m, 1H), 3.66 (s, 3H), 2.78 (t, J = 6.6 Hz, 2H), 2.51 (t, J = 6.6 Hz, 2H), 2.09 (quintuplet, J = 6.6 Hz, 2H). |
| 4 | Light yellow solid | 173-175 | ¹H NMR (600 MHz, CDCl$_3$): δ 16.82 (s, 1H), 8.38 (d, J = 1.8 Hz, 1H), 7.89 (dd, J = 8.4, 1.8 Hz, 1H), 7.49-7.41 (m, 2H), 7.28 (d, J = 8.4 Hz, 2H), 7.19-7.15 (m, 3H), 3.66 (s, 3H), 2.66 (s, 2H), 2.40 (s, 2H), 1.16 (s, 6H). |
| 5 | Light yellow solid | 202-204 | ¹H NMR (600 MHz, CDCl$_3$): δ 16.78 (s, 1H), 8.43 (d, J = 1.8 Hz, 1H), 7.91 (dd, J = 8.4, 1.8 Hz, 1H), 7.59-7.55 (m, 1H), 7.43 (t, J = 3.0 Hz, 1H), 7.41 (t, J = 3.6 Hz, 1H), 7.32 (dt, J = 6.0, 3.6 Hz, 1H), 7.29 (d, J = 8.4 Hz, 1H), 3.68 (s, 3H), 2.77 (t, J = 6.6 Hz, 2H), 2.51 (td, J = 9.6, 3.6 Hz, 2H), 2.09 (quintuplet, J = 6.6 Hz, 2H). |
| 6 | Light yellow solid | 200-202 | ¹H NMR (600 MHz, CDCl$_3$): δ 16.86 (s, 1H), 8.42 (s, 1H), 7.89 (d, J = 8.4 Hz, 1H), 7.60-7.55 (m, 1H), 7.45-7.40 (m, 2H), 7.35-7.31 (m, 1H), 7.29 (d, J = 8.4 Hz, 1H), 3.68 (s, 3H), 2.66 (s, 2H), 2.40 (s, 2H), 1.16 (d, J = 6.0 Hz, 6H). |
| 7 | Light yellow solid | 140-142 | ¹H NMR (600 MHz, CDCl$_3$): δ 16.77 (s, 1H), 8.38 (d, J = 1.8 Hz, 1H), 7.91 (dd, J = 8.4, 1.8 Hz, 1H), 7.46 (t, J = 1.8 Hz, 1H), 7.29 (d, J = 9.0 Hz, 1H), 7.20 (d, J = 1.8 Hz, 2H), 3.66 (s, 3H), 2.78 (t, J = 6.6 Hz, 2H), 2.51 (t, J = 6.6 Hz, 2H), 2.10 (quintuplet, J = 6.6 Hz, 2H). |
| 8 | Light yellow solid | 223-225 | ¹H NMR (600 MHz, CDCl$_3$): δ 16.83 (s, 1H), 8.37 (d, J = 1.8 Hz, 1H), 7.89 (dd, J = 8.4, 1.8 Hz, 1H), 7.46 (t, J = 1.8 Hz, 1H), 7.29 (d, J = 9.0 Hz, 1H), 7.20 (d, J = 1.8 Hz, 2H), 3.66 (s, 3H), 2.67 (s, 2H), 2.40 (s, 2H), 1.16 (s, 6H). |

TABLE 1-continued

| NO. | Appearance | Melting point/° C. | $^1$HNMR |
|---|---|---|---|
| 9 | White solid | 172-174 | $^1$H NMR (600 MHz, CDCl$_3$): δ 16.77 (s, 1H), 8.40 (d, J = 1.8 Hz, 1H), 7.90 (dd, J = 9.0, 1.8 Hz, 1H), 7.28 (d, J = 9.0 Hz, 1H), 7.24 (dd, J = 9.0, 4.8 Hz, 2H), 7.20 (t, J = 8.4 Hz, 2H), 3.66 (s, 3H), 2.77 (t, J = 6.6 Hz, 2H), 2.51 (t, J = 6.6 Hz, 2H), 2.09 (quintuplet, J = 6.6 Hz, 2H). |
| 10 | Light brown solid | 148-150 | $^1$H NMR (600 MHz, CDCl$_3$): δ 16.76 (s, 1H), 8.40 (d, J = 1.8 Hz, 1H), 7.90 (dd, J = 8.4, 1.8 Hz, 1H), 7.48 (dd, J = 14.4, 8.4 Hz, 1H), 7.28 (d, J = 8.4 Hz, 1H), 7.17 (td, J = 8.4, 1.8 Hz, 1H), 7.07 (d, J = 7.8 Hz, 1H), 7.02 (d, J = 9.0 Hz, 1H), 3.67 (s, 3H), 2.77 (t, J = 6.6 Hz, 2H), 2.51 (t, J = 6.6 Hz, 2H), 2.09 (quintuplet, J = 6.6 Hz , 2H). |
| 11 | Light brown solid | 147-149 | $^1$H NMR (600 MHz, CDCl$_3$): δ 16.80 (s, 1H), 8.38 (d, J = 1.8 Hz, 1H), 7.89 (dd, J = 9.0, 1.8 Hz, 1H), 7.48 (dd, J = 14.4, 8.4 Hz, 1H), 7.29 (d, J = 8.4 Hz, 1H), 7.17 (td, J = 8.4, 1.8 Hz, 1H), 7.07 (d, J = 7.8 Hz, 1H), 7.02 (d, J = 9.0 Hz, 1H), 3.67 (s, 3H), 2.66 (s, 2H), 2.40 (s, 2H), 1.14 (s, 6H). |
| 12 | Light brown solid | 148-150 | $^1$H NMR (600 MHz, CDCl$_3$): δ 16.77 (s, 1H), 8.41 (d, J = 1.8 Hz, 1H), 7.90 (dd, J = 8.4, 1.8 Hz, 1H), 7.47-7.43 (m, 1H), 7.33-7.30 (m, 1H), 7.29 (d, J = 8.4 Hz, 2H), 7.25 (t, J = 9.0 Hz, 1H), 3.68 (s, 3H), 2.77 (t, J = 6.6 Hz, 2H), 2.51 (t, J = 6.6 Hz, 2H), 2.09 (quintuplet, J = 6.6 Hz, 2H). |
| 13 | Light brown solid | 192-194 | $^1$H NMR (600 MHz, CDCl$_3$): δ 16.84 (s, 1H), 8.40 (d, J = 1.8 Hz, 1H), 7.89 (dd, J = 8.4, 1.8 Hz, 1H), 7.47-7.43 (m, 1H), 7.33-7.30 (m, 1H), 7.29 (d, J = 8.4 Hz, 2H), 7.24 (t, J = 9.0 Hz, 1H), 3.68 (s, 3H), 2.66 (s, 2H), 2.40 (s, 2H), 1.16 (d, J = 3.6 Hz, 6H). |
| 14 | Light brown solid | 201-203 | $^1$H NMR (600 MHz, CDCl$_3$): δ 16.77 (s, 1H), 8.40 (d, J = 1.8 Hz, 1H), 7.88 (dd, J = 8.4, 1.8 Hz, 1H), 7.31 (d, J = 8.4 Hz, 2H), 7.27 (d, J = 8.4 Hz, 1H), 7.14 (d, J = 8.4 Hz, 2H), 3.66 (s, 3H), 2.77 (t, J = 6.6 Hz, 2H), 2.50 (t, J = 6.6 Hz, 2H), 2.41 (s, 3H), 2.09 (quintuplet, J = 6.6 Hz, 2H). |
| 15 | Light yellow solid | 168-170 | $^1$H NMR (600 MHz, CDCl$_3$): δ 16.82 (s, 1H), 8.39 (d, J = 1.8 Hz, 1H), 7.87 (dd, J = 8.4, 1.8 Hz, 1H), 7.31 (d, J = 8.4 Hz, 2H), 7.27 (d, J = 8.4 Hz, 1H), 7.14 (d, J = 8.4 Hz, 2H), 3.66 (s, 3H), 2.65 (s, 2H), 2.41 (s, 3H), 2.39 (s, 2H), 1.15 (s, 6H). |
| 16 | Light yellow solid | 230-232 | $^1$H NMR (600 MHz, CDCl$_3$): δ 16.76 (s, 1H), 8.40 (d, J = 1.8 Hz, 1H), 7.88 (dd, J = 8.4, 1.8 Hz, 1H), 7.31 (d, J = 8.4 Hz, 2H), 7.27 (d, J = 8.4 Hz, 1H), 7.14 (d, J = 8.4 Hz, 2H), 3.66 (s, 3H), 2.81 (dd, J = 18.0, 2.4 Hz, 1H), 2.59 (dd, J = 16.2, 2.4 Hz, 1H), 2.48 (dd, J = 18.0, 10.8 Hz, 1H), 2.41 (s, 3H), 2.35 (td, J = 17.4, 6.6 Hz, 1H), 2.20 (dd, J = 16.8, 11.4 Hz, 1H), 1.15 (d, J = 6.6 Hz, 3H). |
| 17 | Light yellow solid | 100-102 | $^1$H NMR (600 MHz, CDCl$_3$): δ 16.76 (s, 1H), 8.40 (d, J = 1.8 Hz, 1H), 7.89 (dd, J = 8.4, 1.8 Hz, 1H), 7.40 (t, J = 7.8 Hz, 1H), 7.27 (m, 2H), 7.06 (d, J = 10.2 Hz, 2H), 3.66 (s, 3H), 2.77 (t, J = 6.6 Hz, 2H), 2.51 (t, J = 6.6 Hz, 2H), 2.41 (s, 3H), 2.09 (quintuplet, J = 6.6 Hz, 2H). |
| 18 | Light yellow solid | 183-185 | $^1$H NMR (600 MHz, CDCl$_3$): δ 16.81 (s, 1H), 8.39 (d, J = 1.8 Hz, 1H), 7.88 (dd, J = 8.4, 1.8 Hz, 1H), 7.40 (t, J = 7.8 Hz, 1H), 7.27 (m, 2H), 7.06 (d, J = 10.2 Hz, 2H), 3.66 (s, 3H), 2.66 (s, 2H), 2.40 (s, 3H), 2.39 (s, 2H), 1.15 (s, 6H). |
| 19 | White solid | 140-142 | $^1$H NMR (600 MHz, CDCl$_3$): δ 16.75 (s, 1H), 8.39 (d, J = 1.8 Hz, 1H), 7.88 (dd, J = 8.4, 1.8 Hz, 1H), 7.40 (t, J = 7.8 Hz, 1H), 7.27 (m, 2H), 7.06 (d, J = 9.6 Hz, 2H), 3.66 (s, 3H), 2.81 (dd, J = 18.0, 2.4 Hz, 1H), 2.59 (dd, J = 16.2 Hz, 2.4 Hz, 1H), 2.48 (dd, J = 18.0, 10.8 Hz, 1H), 2.40 (s, 3H), 2.35 (td, J = 17.4, 6.6 Hz, 1H), 2.20 (dd, J = 16.8, 11.4 Hz, 1H), 1.15 (d, J = 6.6 Hz, 3H). |
| 20 | Light yellow solid | 209-211 | $^1$H NMR (600 MHz, CDCl$_3$): δ 16.78 (s, 1H)8.42 (d, J = 1.8 Hz, 1H), 7.90 (dd, J = 8.4, 1.8 Hz, 1H), 7.38-7.35 (m, 2H), 7.35-7.31 (m, 1H), 7.29 (d, J = 8.4 Hz, 1H), 7.14 (d, J = 7.8 Hz, 1H), 3.67 (s, 3H), 2.77 (t, J = 6.6 Hz, 2H), 2.51 (t, J = 6.6 Hz, 2H), 2.16 (s, 3H), 2.09 (quintuplet, J = 6.6 Hz, 2H). |
| 21 | Light yellow solid | 152-154 | $^1$H NMR (600 MHz, CDCl$_3$): δ 16.87 (s, 1H), 8.42 (d, J = 1.8 Hz, 1H), 7.88 (dd, J = 8.4, 1.8 Hz, 1H), 7.38-7.35 (m, 2H), 7.35-7.32 (m, 1H), 7.29 (d, J = 8.4 Hz, 1H), 7.15 (d, J = 7.2 Hz, 1H), 3.68 (s, 3H), 2.67 (s, 2H), 2.41 (s, 2H), 2.16 (s, 3H), 1.16 (d, J = 4.2 Hz, 6H). |
| 22 | Light brown solid | 148-150 | $^1$H NMR (600 MHz, CDCl$_3$): δ 16.82 (s, 1H), 8.38 (d, J = 1.8 Hz, 1H), 7.88 (dd, J = 8.4, 1.8 Hz, 1H), 7.28 (d, J = 8.4 Hz, 1H), 7.24 (dd, J = 9.0, 4.8 Hz, 2H), 7.20 (t, J = 8.4 Hz, 2H), 3.66 (s, 3H), 2.66 (s, 2H), 2.40 (s, 2H), 1.16 (s, 6H). |
| 23 | Light yellow solid | 137-139 | $^1$H NMR (600 MHz, CDCl$_3$): δ 16.77 (s, 1H), 8.39 (d, J = 1.8 Hz, 1H), 7.90 (dd, J = 8.4, 1.8 Hz, 1H), 7.59 (d, J = |

TABLE 1-continued

| NO. | Appearance | Melting point/° C. | ¹HNMR |
|---|---|---|---|
|  |  |  | 8.4 Hz, 1H), 7.44 (s, 1H), 7.39 (t, J = 7.8 Hz, 1H), 7.28 (d, J = 8.4 Hz, 1H), 7.22 (d, J = 7.8 Hz, 1H), 3.66 (s, 3H), 2.78 (t, J = 6.6 Hz, 2H), 2.51 (t, J = 6.6 Hz, 2H), 2.09 (quintuplet, J = 6.6 Hz, 2H). |
| 24 | Light yellow solid | 167-169 | ¹H NMR (600 MHz, CDCl$_3$): δ 16.83 (s, 1H), 8.38 (d, J = 1.8 Hz, 1H), 7.89 (dd, J = 8.4, 1.8 Hz, 1H), 7.59 (d, J = 8.4 Hz, 1H), 7.44 (s, 1H), 7.39 (t, J = 7.8 Hz, 1H), 7.28 (d, J = 7.8 Hz, 1H), 7.22 (d, J = 8.1 Hz, 1H), 3.66 (s, 3H), 2.66 (s, 2H), 2.40 (s, 2H), 1.16 (s, 6H). |
| 25 | Light yellow solid | 225-227 | ¹H NMR (600 MHz, CDCl$_3$): δ 16.79 (s, 1H), 8.39 (d, J = 1.8 Hz, 1H), 7.90 (dd, J = 9.0, 1.8 Hz, 1H), 7.64 (d, J = 8.4 Hz, 2H), 7.29 (d, J = 8.4 Hz, 1H), 7.15 (d, J = 8.4 Hz, 2H), 3.66 (s, 3H), 2.78 (t, J = 6.6 Hz, 2H), 2.51 (t, J = 6.6 Hz, 2H), 2.09 (quintuplet, J = 6.6 Hz, 2H). |
| 26 | Light yellow solid | 134-136 | ¹H NMR (600 MHz, CDCl$_3$): δ 16.82 (s, 1H), 8.38 (d, J = 1.8 Hz, 1H), 7.88 (dd, J = 9.0, 1.8 Hz, 1H), 7.64 (d, J = 8.4 Hz, 2H), 7.28 (d, J = 9.0 Hz, 1H), 7.14 (d, J = 8.4 Hz, 2H), 3.66 (s, 3H), 2.66 (s, 2H), 2.39 (s, 2H), 1.15 (s, 6H). |
| 27 | Light yellow solid | 212-214 | ¹H NMR (600 MHz, CDCl$_3$): δ 16.78 (s, 1H), 8.43 (d, J = 1.8 Hz, 1H), 7.91 (dd, J = 9.0, 1.8 Hz, 1H), 7.74 (d, J = 7.8 Hz, 1H), 7.47 (t, J = 7.8 Hz, 1H), 7.37-7.28 (m, 3H), 3.68 (s, 3H), 2.77 (t, J = 6.0 Hz, 2H), 2.51 (dd, J = 10.8, 6.0 Hz, 2H), 2.12-2.06 (m, 2H). |
| 28 | Light yellow solid | 225-227 | ¹H NMR (600 MHz, CDCl$_3$): δ 16.87 (s, 1H), 8.42 (d, J = 1.8 Hz, 1H), 7.88 (dd, J = 8.4, 1.8 Hz, 1H), 7.74 (d, J = 7.8 Hz, 1H), 7.47 (t, J = 7.2 Hz, 1H), 7.37-7.28 (m, 3H), 3.67 (s, 3H), 2.70-2.61 (m, 2H), 2.43-2.35 (m, 2H), 1.15 (d, J = 8.4 Hz, 6H). |
| 29 | Light yellow solid | 185-184 | ¹H NMR (600 MHz, CDCl$_3$): δ 16.77 (s, 1H), 8.41 (d, J = 1.2 Hz, 1H), 7.88 (dd, J = 8.4, 1.2 Hz, 1H), 7.42 (t, J = 7.2 Hz, 1H), 7.27 (d, J = 8.4 Hz, 1H), 7.20 (dd, J = 7.8, 1.2 Hz, 1H), 7.20-7.10 (m, 2H), 3.78 (s, 3H), 3.65 (s, 3H), 2.75 (t, J = 6.0 Hz, 2H), 2.50 (t, J = 6.6 Hz, 2H), 2.07 (quintuplet, J = 6.6 Hz, 2H). |
| 30 | White solid | 236-238 | ¹H NMR (600 MHz, CDCl$_3$): δ 16.79 (s, 1H), 8.40 (d, J = 1.8 Hz, 1H), 7.92 (dd, J = 9.0, 1.8 Hz, 1H), 7.79 (d, J = 8.4 Hz, 2H), 7.41 (d, J = 8.4 Hz, 2H), 7.30 (d, J = 8.4 Hz, 1H), 3.68 (s, 3H), 2.78 (t, J = 6.6 Hz, 2H), 2.51 (t, J = 6.6 Hz, 2H), 2.10 (quintuplet, J = 6.6 Hz, 2H). |
| 31 | White solid | 162-164 | ¹H NMR (600 MHz, CDCl$_3$): δ 16.83 (s, 1H), 8.39 (s, 1H), 7.90 (d, J = 7.8 Hz, 1H), 7.79 (d, J = 8.4 Hz, 2H), 7.42 (d, J = 7.8 Hz, 2H), 7.30 (d, J = 9.0 Hz, 1H), 3.68 (s, 3H), 2.67 (s, 2H), 2.40 (s, 2H), 1.16 (s, 7H). |
| 32 | White solid | 200-202 | ¹H NMR (600 MHz, CDCl$_3$): δ 16.79 (s, 1H), 8.45 (s, 1H), 7.90 (d, J = 8.4 Hz, 1H), 7.47 (d, J = 7.8 Hz, 2H), 7.35 (t, J = 7.8 Hz, 1H), 7.30 (d, J = 8.4 Hz, 1H), 3.68 (s, 3H), 2.76 (t, J = 6.6 Hz, 2H), 2.51 (t, J = 6.6 Hz, 2H), 2.08 (quintuplet, J = 6.6 Hz, 2H). |
| 33 | Yellow solid | 202-204 | ¹H NMR (600 MHz, CDCl$_3$): δ 16.80 (s, 1H), 8.41 (d, J = 1.8 Hz, 1H), 7.91 (dd, J = 8.4, 1.8 Hz, 1H), 7.34 (dd, J = 8.4, 1.8 Hz, 1H), 7.29 (d, J = 8.4 Hz, 2H), 7.17 (d, J = 1.8 Hz, 1H), 3.67 (s, 3H), 2.78 (t, J = 6.6 Hz, 2H), 2.52 (t, J = 6.6 Hz, 2H), 2.12 (s, 3H), 2.10 (quintuplet, J = 6.6 Hz, 2H). |
| 34 | Yellow solid | 187-189 | ¹H NMR (600 MHz, CDCl$_3$): δ 16.83 (s, 1H), 8.45 (d, J = 1.8 Hz, 1H), 7.90 (dd, J = 9.0, 1.8 Hz, 1H), 7.29 (d, J = 9.0 Hz, 1H), 7.24 (d, J = 7.2 Hz, 1H), 7.18 (d, J = 7.2 Hz, 2H), 3.69 (s, 3H), 2.78 (t, J = 6.0 Hz, 2H), 2.52 (t, J = 6.6 Hz, 2H), 2.14-2.06 (m, 8H). |
| 35 | White solid | 125-127 | ¹H NMR (600 MHz, CDCl$_3$): δ 16.76 (s, 1H), 8.40 (d, J = 1.8 Hz, 1H), 7.90 (dd, J = 9.0, 1.8 Hz, 1H), 7.52 (d, J = 7.8 Hz, 2H), 7.45 (t, J = 7.2 Hz, 1H), 7.30-7.24 (m, 3H), 3.67 (s, 3H), 2.77 (t, J = 6.0 Hz, 2H), 2.51 (t, J = 6.0 Hz, 2H), 2.09 (quintuplet, J = 6.0 Hz, 2H). |
| 36 | White solid | 206-208 | ¹H NMR (600 MHz, CDCl$_3$): δ 16.76 (s, 1H), 8.40 (d, J = 1.8 Hz, 1H), 7.89 (dd, J = 9.0, 1.8 Hz, 1H), 7.36 (d, J = 8.4 Hz, 2H), 7.28 (d, J = 8.0 Hz, 1H), 7.17 (d, J = 7.8 Hz, 2H), 3.67 (s, 3H), 2.98 (dq, J = 13.8, 6.6 Hz, 1H), 2.77 (t, J = 6.0 Hz, 2H), 2.51 (t, J = 6.6 Hz, 2H), 2.09 (quintuplet, J = 6.6 Hz, 2H), 1.29 (d, J = 6.6 Hz, 6H). |
| 37 | Light yellow solid | 133-235 | ¹H NMR (600 MHz, CDCl$_3$): δ 16.85 (s, 1H), 8.40 (d, J = 1.8 Hz, 1H), 7.89 (dd, J = 8.4, 1.8 Hz, 1H), 7.34 (dd, J = 8.4, 1.8 Hz, 1H), 7.29 (d, J = 8.4 Hz, 2H), 7.17 (d, J = 1.8 Hz, 1H), 3.67 (s, 3H), 2.66 (s, 2H), 2.40 (s, 2H), 2.12 (s, 3H), 1.16 (s, 6H). |
| 38 | Light yellow solid | 199-201 | ¹H NMR (600 MHz, CDCl$_3$): δ: 16.81 (s, 1H), 8.42 (s, 1H), 7.92 (d, J = 8.4 Hz, 1H), 7.84 (d, J = 7.8 Hz, 1H), 7.73 (t, J = 7.8 Hz, 1H), 7.62 (t, J = 7.8 Hz, 1H), 7.35 (d, |

TABLE 1-continued

| NO. | Appearance | Melting point/° C. | ¹HNMR |
|---|---|---|---|
| | | | J = 7.8 Hz, 1H), 7.30 (d, J = 9.0 Hz, 1H), 3.67 (s, 3H), 2.78 (t, J = 6.0 Hz, 2H), 2.57-2.46 (m, 2H), 2.09 (quintuplet, J = 6.0 Hz, 2H). |
| 39 | Light yellow solid | 98-100 | ¹H NMR (600 MHz, CDCl₃): δ 16.78 (s, 1H), 8.42 (d, J = 1.8 Hz, 1H), 7.91 (dd, J = 9.0, 1.8 Hz, 1H), 7.51 (t, J = 7.8 Hz, 1H), 7.43 (dd, J = 12.6, 6.6 Hz, 2H), 7.35 (d, J = 7.8 Hz, 1H), 7.29 (d, J = 8.4 Hz, 1H), 3.67 (s, 3H), 2.77 (t, J = 6.0 Hz, 2H), 2.56-2.45 (m, 2H), 2.09 (quintuplet, J = 6.0 Hz, 2H). |
| 40 | Light yellow solid | 175-177 | ¹H NMR (600 MHz, CDCl₃): δ 16.84 (s, 1H), 8.39 (s, 1H), 7.89 (d, J = 8.4 Hz, 1H), 7.53 (t, J = 7.8 Hz, 2H), 7.46 (t, J = 7.8 Hz, 1H), 7.29 (d, J = 8.4 Hz, 1H), 7.27 (d, J = 8.4), 3.67 (s, 3H), 2.66 (s, 2H), 2.40 (s, 2H), 1.16 (s, 6H). |
| 41 | White solid | 221-223 | ¹H NMR (600 MHz, CDCl₃): δ 16.90 (s, 1H), 8.41 (s, 1H), 7.89 (d, J = 8.4 Hz, 1H), 7.84 (d, J = 7.8 Hz, 1H), 7.73 (t, J = 7.8 Hz, 1H), 7.62 (t, J = 7.8 Hz, 1H), 7.35 (d, J = 7.8 Hz, 1H), 7.30 (d, J = 9.0 Hz, 1H), 3.67 (s, 3H), 2.70 (t, J = 1.8 Hz, 2H), 2.41 (dd, J = 23.4, 16.2 Hz, 2H), 1.16 (d, J = 10.2 Hz, 6H). |
| 42 | Light yellow solid | 186-188 | ¹H NMR (600 MHz, CDCl₃): δ 16.75 (s, 1H), 8.40 (d, J = 1.8 Hz, 1H), 7.89 (dd, J = 9.0, 1.8 Hz, 1H), 7.52 (t, J = 7.8 Hz, 2H), 7.45 (t, J = 7.8 Hz, 1H), 7.27 (t, J = 9.0 Hz, 3H), 3.67 (s, 3H), 2.81 (ddd, J = 18.6, 4.2, 1.8 Hz, 1H), 2.59 (ddd, J = 16.8, 3.6, 1.8 Hz, 1H), 2.48 (dd, J = 18.0, 10.8 Hz, 1H), 2.40-2.31 (m, 1H), 2.20 (dd, J = 16.8, 11.4 Hz, 1H), 1.15 (d, J = 6.6 Hz, 3H). |
| 43 | Light yellow solid | 231-233 | ¹H NMR (600 MHz, CDCl₃): δ 16.76 (s, 1H), 8.40 (d, J = 1.8 Hz, 1H), 7.90 (dd, J = 8.4, 1.8 Hz, 1H), 7.48 (d, J = 8.4 Hz, 2H), 7.28 (d, J = 8.4 Hz, 1H), 7.22 (d, J = 9.0 Hz, 2H), 4.24 (q, J = 7.2 Hz, 2H), 2.77 (t, J = 6.0 Hz, 2H), 2.51 (t, J = 6.6 Hz, 2H), 2.09 (quintuplet, J = 6.0 Hz, 2H), 1.40 (t, J = 6.6 Hz, 3H). |
| 44 | White solid | 200-202 | ¹H NMR (600 MHz, CDCl₃): δ 16.78 (s, 1H), 8.44 (d, J = 1.8 Hz, 1H), 7.98 (d, J = 8.4 Hz, 1H), 7.94 (d, J = 7.8 Hz, 2H), 7.59 (dd, J = 15.6, 7.8 Hz, 2H), 7.49 (dt, J = 19.8, 7.2 Hz, 2H), 7.44 (d, J = 7.2 Hz, 1H), 7.35 (d, J = 9.0 Hz, 1H), 3.71 (s, 3H), 2.77 (t, J = 6.0 Hz, 2H), 2.51 (t, J = 6.0 Hz, 2H), 2.081 (quintuplet, J = 6.0 Hz, 2H). |
| 45 | Yellow solid | 242-244 | ¹H NMR (600 MHz, CDCl₃): δ 16.79 (s, 1H), 8.40 (s, 2H), 8.38 (s, 1H), 7.93 (dd, J = 9.0, 1.8 Hz, 1H), 7.49 (d, J = 8.4 Hz, 2H), 7.32 (d, J = 9.0 Hz, 1H), 3.68 (s, 3H), 2.79 (t, J = 6.0 Hz, 2H), 2.52 (t, J = 6.6 Hz, 2H), 2.10 (quintuplet, J = 6.6 Hz, 2H). |
| 46 | White solid | 128-130 | ¹H NMR (600 MHz, CDCl₃): δ 16.90 (s, 1H), 8.47 (s, 1H), 7.88 (d, J = 8.4 Hz, 1H), 7.44 (t, J = 7.8 Hz, 1H), 7.29 (d, J = 7.2 Hz, 3H), 3.69 (s, 3H), 2.78 (t, J = 6.0 Hz, 2H), 2.68-2.59 (m, 2H), 2.53 (t, J = 6.6 Hz, 2H), 2.10 (quintuplet, J = 6.6 Hz, 2H), 1.16 (dd, J = 12.0, 6.6 Hz, 12H). |
| 47 | White solid | 129-131 | ¹H NMR (600 MHz, CDCl₃): δ 16.79 (s, 1H), 8.44 (s, 1H), 7.90 (d, J = 9.0 Hz, 1H), 7.41 (s, 2H), 7.36-7.30 (m, 1H), 7.28 (d, J = 8.4 Hz, 1H), 7.12 (d, J = 7.8 Hz, 1H), 3.67 (s, 3H), 2.77 (t, J = 6.0 Hz, 2H), 2.51 (t, J = 6.6 Hz, 2H), 2.47 (q, J = 7.8 Hz, 2H), 2.08 (quintuplet, J = 6.6 Hz, 2H), 1.17 (t, J = 7.8 Hz, 3H). |
| 48 | Light yellow solid | 223-225 | ¹H NMR (600 MHz, CDCl₃): δ 16.85 (s, 1H), 8.40 (d, J = 1.8 Hz, 1H), 7.86 (dd, J = 9.0, 1.8 Hz, 1H), 7.45-7.40 (m, 1H), 7.27 (d, J = 9.0 Hz, 2H), 7.20 (dd, J = 7.8, 1.2 Hz, 1H), 7.07 (t, J = 7.8 Hz, 1H), 7.05 (d, J = 8.4 Hz, 1H), 3.79 (s, 3H), 3.66 (s, 3H), 2.65 (s, 2H), 2.40 (s, 2H), 1.15 (d, J = 4.2 Hz, 6H). |
| 49 | White solid | 137-139 | ¹H NMR (600 MHz, CDCl₃): δ 16.81 (s, 1H), 8.38 (d, J = 1.8 Hz, 1H), 7.89 (dd, J = 9.0, 1.8 Hz, 1H), 7.36 (d, J = 8.4 Hz, 2H), 7.31 (d, J = 9.0 Hz, 2H), 7.29 (d, J = 9.0 Hz, 1H), 3.67 (s, 3H), 2.66 (s, 2H), 2.40 (s, 2H), 1.16 (s, 6H). |
| 50 | Light yellow solid | 222-224 | ¹H NMR (600 MHz, CDCl₃): δ 16.75 (s, 1H), 8.39 (s, 1H), 7.91 (d, J = 8.4 Hz, 1H), 7.36 (d, J = 7.8 Hz, 2H), 7.33-7.27 (m, 3H), 3.67 (s, 3H), 2.77 (t, J = 6.0 Hz, 2H), 2.51 (t, J = 6.0 Hz, 2H), 2.09 (quintuplet, J = 6.0 Hz, 2H). |
| 51 | White solid | 150-152 | ¹H NMR (600 MHz, CDCl₃): δ 16.83 (s, 1H), 8.39 (s, 1H), 7.90 (d, J = 9.0 Hz, 1H), 7.72 (d, J = 7.8 Hz, 1H), 7.65 (t, J = 7.8 Hz, 1H), 7.57 (s, 1H), 7.47 (d, J = 7.8 Hz, 1H), 7.30 (d, J = 9.0 Hz, 1H), 3.67 (s, 3H), 2.66 (s, 2H), 2.40 (s, 2H), 1.16 (s, 6H). |
| 52 | Light yellow solid | 116-118 | ¹H NMR (600 MHz, CDCl₃): δ 16.76 (s, 1H), 8.39 (d, J = 1.8 Hz, 1H), 7.91 (dd, J = 8.4, 1.8 Hz, 1H), 7.72 (d, J = 7.8 Hz, 1H), 7.64 (t, J = 7.8 Hz, 1H), 7.56 (s, 1H), 7.47 |

TABLE 1-continued

| NO. | Appearance | Melting point/° C. | ¹HNMR |
|---|---|---|---|
| | | | (d, J = 7.8 Hz, 1H), 7.29 (d, J = 9.0 Hz, 1H), 3.66 (s, 3H), 2.77 (t, J = 6.6 Hz, 2H), 2.50 (t, J = 6.6 Hz, 2H), 2.08 (quintuplet, J = 6.0 Hz, 2H). |
| 53 | Light yellow solid | 172-174 | ¹H NMR (600 MHz, CDCl₃): δ 16.84 (s, 1H), 8.41-7.36 (m, 3H), 7.90 (dd, J = 9.0, 1.8 Hz, 1H), 7.48 (d, J = 9.0 Hz, 2H), 7.31 (d, J = 8.4 Hz, 2H), 3.68 (s, 3H), 2.67 (s, 2H), 2.40 (s, 2H), 1.16 (s, 6H). |
| 54 | Beige solid | 217-219 | ¹H NMR (600 MHz, CDCl₃): δ 17.26 (s, 0.4H), 16.45 (s, 0.6H), 8.43 (d, J = 2.4 Hz, 0.4H), 8.37 (d, J = 2.4 Hz, 0.6H), 7.90 (dd, J = 9.0, 2.4 Hz, 0.4H), 7.85 (dd, J = 9.0, 2.4 Hz, 0.6H), 7.48 (s, 1H), 7.46 (s, 1H), 7.37-7.33 (m, 1H), 7.33-7.28 (m, 1H), 3.68 (s, 3H), 2.79 (t, J = 6.6 Hz, 1.4H), 2.55 (t, J = 6.6 Hz, 0.6H), 1.94 (t, J = 6.6 Hz, 0.6H), 1.91 (t, J = 6.6 Hz, 1.4H), 1.38 (s, 2H), 1.20 (s, 4H). |
| 55 | White solid | 176-178 | ¹H NMR (600 MHz, CDCl₃): δ 16.76 (s, 1H), 8.40 (s, 1H), 7.90 (d, J = 9.0 Hz, 1H), 7.42 (t, J = 7.8 Hz, 1H), 7.28 (d, J = 8.4 Hz, 1H), 7.00 (d, J = 9.0 Hz, 1H), 6.85 (d, J = 7.8 Hz, 1H), 6.80 (s, 1H), 3.82 (s, 3H), 3.67 (s, 3H), 2.77 (t, J = 6.0 Hz, 2H), 2.51 (t, J = 6.0 Hz, 2H), 2.09 (quintuplet, J = 6.0 Hz, 2H). |
| 56 | White solid | 223-225 | ¹H NMR (600 MHz, CDCl₃): δ 16.81 (s, 1H), 8.39 (d, J = 2.4 Hz, 1H), 7.88 (dd, J = 9.0, 2.4 Hz, 1H), 7.42 (t, J = 8.4 Hz, 1H), 7.28 (d, J = 8.4 Hz, 1H), 7.00 (dd, J = 8.4, 2.4 Hz, 1H), 6.87-6.83 (m, 1H), 6.80 (t, J = 2.4 Hz, 1H), 3.82 (s, 3H), 3.67 (s, 3H), 2.66 (s, 2H), 2.39 (s, 2H), 1.15 (s, 6H). |
| 57 | White solid | 201-203 | ¹H NMR (600 MHz, CDCl₃): δ 16.77 (s, 1H), 8.40 (d, J = 1.8 Hz, 1H), 7.89 (dd, J = 9.0, 2.4 Hz, 1H), 7.27 (d, J = 8.4 Hz, 1H), 7.24-7.12 (m, 2H), 7.06-6.97 (m, 2H), 3.85 (s, 3H), 3.66 (s, 3H), 2.77 (t, J = 6.0 Hz, 2H), 2.51 (t, J = 6.6 Hz, 2H), 2.09 (quintuplet, J = 6.0 Hz, 2H). |
| 58 | Light yellow solid | 143-145 | ¹H NMR (600 MHz, CDCl₃): δ 16.82 (s, 1H), 8.39 (d, J = 1.8 Hz, 1H), 7.87 (dd, J = 9.0, 1.8 Hz, 1H), 7.27 (d, J = 7.8 Hz, 2H), 7.17 (d, J = 8.4 Hz, 2H), 7.02 (d, J = 9.0 Hz, 2H), 3.85 (s, 3H), 3.66 (s, 3H), 2.65 (s, 2H), 2.39 (s, 2H), 1.15 (s, 6H). |
| 59 | Light yellow solid | 236-238 | ¹H NMR (600 MHz, CDCl₃): δ 16.83 (s, 1H), 10.23 (s, 1H), 8.30 (d, J = 1.8 Hz, 1H), 7.60 (dd, J = 8.4, 1.8 Hz, 1H), 7.42-7.38 (m, 2H), 7.38-7.34 (m, 1H), 7.19 (d, J = 7.8 Hz, 1H), 6.68 (d, J = 8.4 Hz, 1H), 2.63 (s, 2H), 2.42 (s, 2H), 2.18 (s, 3H), 1.15 (d, J = 2.8 Hz, 6H). |
| 60 | Light yellow solid | 135-137 | ¹H NMR (600 MHz, CDCl₃): δ 16.79 (s, 1H), 8.41 (d, J = 1.8 Hz, 1H), 7.92 (dd, J = 9.0, 1.8 Hz, 1H), 7.69 (q, J = 8.4 Hz, 2H), 7.61 (s, 1H), 7.31 (d, J = 8.4 Hz, 1H), 3.68 (s, 3H), 2.77 (brs, 2H), 2.51 (brs, 2H), 2.09 (quintuplet, J = 6.6 Hz, 2H). |
| 61 | Light brown solid | 128-130 | ¹H NMR (600 MHz, CDCl₃): δ 16.88 (s, 1H), 8.41 (d, J = 1.2 Hz, 1H), 7.91 (dd, J = 8.4, 1.8 Hz, 1H), 7.74-7.66 (m, 2H), 7.61 (s, 1H), 7.32 (d, J = 8.4 Hz, 1H), 3.69 (s, 3H), 2.67 (s, 2H), 2.46-2.35 (m, 2H), 1.16 (d, J = 7.8 Hz, 6H). |
| 62 | Light yellow solid | 166-168 | ¹H NMR (600 MHz, CDCl₃): δ 16.80 (s, 1H), 8.41 (d, J = 1.8 Hz, 1H), 7.91 (dd, J = 8.4, 1.8 Hz, 1H), 7.59 (d, J = 1.8 Hz, 1H), 7.40 (dd, J = 8.4, 1.8 Hz, 1H), 7.30 (d, J = 9.0 Hz, 1H), 7.25 (d, J = 8.4 Hz, 1H), 3.68 (s, 3H), 2.78 (t, J = 6.0 Hz, 2H), 2.56-2.46 (m, 2H), 2.10 (quintuplet, J = 6.0 Hz, 2H). |
| 63 | Light yellow solid | 159-161 | ¹H NMR (600 MHz, CDCl₃): δ 16.88 (s, 1H), 8.40 (d, J = 2.4 Hz, 1H), 7.89 (dd, J = 8.4, 2.0 Hz, 1H), 7.59 (d, J = 2.4 Hz, 1H), 7.40 (dd, J = 8.4, 2.4 Hz, 1H), 7.30 (d, J = 9.0 Hz, 1H), 7.25 (d, J = 8.4 Hz, 1H), 3.68 (s, 3H), 2.67 (s, 2H), 2.44-2.37 (m, 2H), 1.16 (d, J = 7.2 Hz, 6H). |
| 64 | Light yellow solid | 179-181 | ¹H NMR (600 MHz, CDCl₃): δ 16.80 (d, J = 14.4 Hz, 1H), 8.41 (s, 1H), 7.93-7.87 (m, 1H), 7.59 (d, J = 1.8 Hz, 1H), 7.42-7.38 (m, 1H), 7.31-7.28 (m, 1H), 7.26-7.23 (m, 1H), 3.68 (s, 3H), 2.88-2.79 (m, 1H), 2.64-2.56 (m, 1H), 2.54-2.45 (m, 1H), 2.40-2.32 (m, 1H), 2.27-2.15 (m, 1H), 1.15 (dd, J = 6.6, 3.0 Hz, 3H). |
| 65 | White solid | 162-164 | ¹H NMR (600 MHz, CDCl₃): δ 16.81 (s, 1H), 8.43 (d, J = 1.2 Hz, 1H), 7.89 (dd, J = 8.4, 1.8 Hz, 1H), 7.49-7.43 (m, 2H), 7.34-7.30 (m, 1H), 7.29 (d, J = 8.4 Hz, 1H), 7.10 (d, J = 7.8 Hz, 1H), 3.67 (s, 4H), 2.77 (t, J = 6.0 Hz, 2H), 2.73 (dt, J = 13.2, 7.2 Hz, 1H), 2.56-2.48 (m, 2H), 2.09 (quintuplet, J = 6.6 Hz, 2H), 1.18 (dd, J = 10.2, 6.6 Hz, 7H). |
| 66 | Light yellow solid | 146-148 | ¹H NMR (600 MHz, CDCl₃): δ 16.79 (s, 1H), 8.44 (d, J = 1.2 Hz, 1H), 7.90 (dd, J = 8.4, 1.2 Hz, 1H), 7.38-7.31 |

TABLE 1-continued

| NO. | Appearance | Melting point/° C. | ¹HNMR |
|---|---|---|---|
| | | | (m, 3H), 7.30 (d, J = 9.0 Hz, 1H), 7.16 (d, J = 7.8 Hz, 1H), 4.26 (q, J = 7.2 Hz, 2H), 2.77 (t, J = 6.0 Hz, 2H), 2.52 (t, J = 6.0 Hz, 2H), 2.15 (s, 3H), 2.09 (quintuplet, J = 6.6 Hz, 2H), 1.40 (t, J = 7.2 Hz, 3H). |
| 67 | White solid | 232-234 | ¹H NMR (600 MHz, CDCl$_3$): δ 16.84 (s, 1H), 8.45 (s, 1H), 7.89 (d, J = 8.4 Hz, 1H), 7.28 (d, J = 8.4 Hz, 1H), 6.99 (s, 2H), 3.68 (s, 3H), 2.77 (s, 2H), 2.52 (s, 2H), 2.32 (s, 3H), 2.09 (s, 2H), 2.07 (s, 6H). |
| 68 | Light yellow solid | 266-268 | ¹H NMR (600 MHz, CDCl$_3$): δ 16.80 (s, 1H), 9.89 (s, 1H), 8.33 (d, J = 1.8 Hz, 1H), 7.68 (dd, J = 8.4, 1.8 Hz, 1H), 7.44-7.29 (m, 3H), 7.19 (d, J = 7.8 Hz, 1H), 6.82 (d, J = 8.4 Hz, 1H), 2.75 (t, J = 6.0 Hz, 2H), 2.53 (t, J = 6.0 Hz, 2H), 2.18 (s, 3H), 2.07 (quintuplet, J = 6.6 Hz, 2H). |
| 69 | Light brown solid | 193-195 | ¹H NMR (600 MHz, CDCl$_3$): δ 16.86 (s, 1H), 8.42 (d, J = 1.8 Hz, 1H), 7.88 (dd, J = 8.4, 1.8 Hz, 1H), 7.38-7.31 (m, 3H), 7.30 (d, J = 9.0 Hz, 1H), 7.16 (d, J = 7.2 Hz, 1H), 4.30-4.22 (m, 2H), 2.66 (s, 2H), 2.41 (s, 2H), 2.15 (s, 3H), 1.40 (t, J = 7.2 Hz, 3H), 1.16 (d, J = 5.4 Hz, 6H). |
| 70 | Light brown solid | 188-190 | ¹H NMR (600 MHz, CDCl$_3$): δ 16.79 (d, J = 14.4 Hz, 1H), 8.43 (s, 1H), 7.89 (d, J = 8.4 Hz, 1H), 7.40-7.32 (m, 3H), 7.29 (d, J = 8.4 Hz, 1H), 7.16 (dd, J = 7.2, 4.2 Hz, 1H), 4.32-4.22 (m, 2H), 2.86-2.78 (m, 1H), 2.60 (d, J = 15.6 Hz, 1H), 2.53-2.44 (m, 1H), 2.41-2.31 (m, 1H), 2.27-2.17 (m, 1H), 2.15 (d, J = 5.4 Hz, 3H), 1.40 (t, J = 7.2 Hz, 3H), 1.15 (dd, J = 7.2, 1.2 Hz, 3H). |
| 71 | Light brown solid | 188-190 | ¹H NMR (600 MHz, CDCl$_3$): δ 16.79 (s, 1H), 8.43 (d, J = 1.2 Hz, 1H), 7.89 (dd, J = 9.0, 1.2 Hz, 1H), 7.38-7.30 (m, 3H), 7.26 (d, J = 9.0 Hz, 1H), 7.15 (d, J = 7.2 Hz, 1H), 4.23-4.08 (m, 2H), 2.77 (t, J = 6.0 Hz, 2H), 2.52 (t, J = 6.0 Hz, 2H), 2.15 (s, 3H), 2.09 (quintuplet, J = 6.6 Hz, 2H), 1.86-1.79 (m, 2H), 1.04 (t, J = 7.2 Hz, 3H). |
| 72 | Light brown solid | 178-180 | ¹H NMR (600 MHz, CDCl$_3$): δ 16.86 (s, 1H), 8.42 (s, 1H), 7.87 (d, J = 8.4 Hz, 1H), 7.39-7.30 (m, 3H), 7.26 (d, J = 9.0 Hz, 3H), 7.15 (d, J = 7.2 Hz, 1H), 4.16 (m, 2H), 2.66 (s, 2H), 2.41 (s, 2H), 2.15 (s, 3H), 1.83 (dd, J = 14.4, 7.2 Hz, 2H), 1.16 (d, J = 5.4 Hz, 6H), 1.04 (t, J = 7.2 Hz, 3H). |
| 73 | Light yellow solid | 156-158 | ¹H NMR (600 MHz, CDCl$_3$): δ 16.80 (s, 1H), 8.44 (d, J = 1.8 Hz, 1H), 7.89 (dd, J = 9.0, 1.8 Hz, 1H), 7.38-7.31 (m, 3H), 7.27 (d, J = 9.0 Hz, 4H), 7.15 (d, J = 7.8 Hz, 1H), 4.24-4.12 (m, 2H), 2.78 (t, J = 6.0 Hz, 2H), 2.52 (t, J = 6.6 Hz, 2H), 2.15 (s, 3H), 2.09 (quintuplet, J = 6.6 Hz, 2H), 1.82-1.74 (m, 2H), 1.51-1.43 (m, 2H), 1.00 (t, J = 7.2 Hz, 3H). |
| 74 | White solid | 197-199 | ¹H NMR (600 MHz, CDCl$_3$): δ 16.87 (s, 1H), 8.42 (d, J = 1.8 Hz, 1H), 7.88 (dd, J = 9.0, 1.8 Hz, 1H), 7.38-7.30 (m, 3H), 7.27 (d, J = 9.0 Hz, 2H), 7.15 (d, J = 7.2 Hz, 1H), 4.28-4.09 (m, 2H), 2.66 (s, 2H), 2.45-2.37 (m, 2H), 2.15 (s, 3H), 1.81-1.74 (m, 2H), 1.50-1.43 (m, 2H), 1.16 (d, J = 5.4 Hz, 6H), 1.00 (t, J = 7.8 Hz, 3H). |
| 75 | White solid | 198-200 | ¹H NMR (600 MHz, CDCl$_3$): δ 16.80 (s, 1H), 8.44 (d, J = 1.8 Hz, 1H), 7.88 (dd, J = 8.4, 1.8 Hz, 1H), 7.39-7.31 (m, 3H), 7.25 (d, J = 9.0 Hz, 1H), 7.14 (d, J = 7.2 Hz, 1H), 4.15 (dd, J = 14.4, 8.4 Hz, 1H), 3.97 (dd, J = 14.4, 6.6 Hz, 1H), 2.78 (t, J = 6.6 Hz, 2H), 2.57-2.47 (m, 2H), 2.30-2.21 (m, 1H), 2.15 (s, 3H), 2.09 (quintuplet, J = 6.6 Hz, 2H), 1.03 (dd, J = 19.2, 6.6 Hz, 6H). |
| 76 | Light brown solid | 170-172 | ¹H NMR (600 MHz, CDCl$_3$): δ 16.88 (s, 1H), 8.43 (d, J = 1.8 Hz, 1H), 7.86 (dd, J = 9.0, 1.8 Hz, 1H), 7.39-7.32 (m, 3H), 7.25 (d, J = 9.0 Hz, 1H), 7.14 (d, J = 7.8 Hz, 1H), 4.15 (dd, J = 14.4, 8.4 Hz, 1H), 3.97 (dd, J = 14.4, 6.6 Hz, 1H), 2.72-2.61 (m, 2H), 2.48-2.37 (m, 2H), 2.31-2.19 (m, 1H), 2.15 (s, 3H), 1.16 (d, J = 5.4 Hz, 6H), 1.03 (dd, J = 19.2, 6.6 Hz, 6H). |
| 77 | White solid | 171-173 | ¹H NMR (600 MHz, CDCl$_3$): δ 16.78 (s, 1H), 8.43 (d, J = 1.8 Hz, 1H), 7.93 (dd, J = 9.0, 1.8 Hz, 1H), 7.47 (d, J = 8.4 Hz, 1H), 7.39-7.31 (m, 3H), 7.17 (d, J = 7.8 Hz, 1H), 5.00 (qd, J = 18.0, 1.8 Hz, 2H), 2.78 (t, J = 6.0 Hz, 2H), 2.52 (t, J = 6.0 Hz, 2H), 2.35 (s, 3H), 2.16 (s, 3H), 2.10 (quintuplet, J = 6.6 Hz, 2H). |
| 78 | Light brown solid | 205-207 | ¹H NMR (600 MHz, CDCl$_3$): δ 16.85 (s, 1H), 8.41 (d, J = 1.8 Hz, 1H), 7.92 (dd, J = 9.0, 1.8 Hz, 1H), 7.47 (d, J = 9.0 Hz, 1H), 7.40-7.31 (m, 3H), 7.17 (d, J = 7.8 Hz, 1H), 5.00 (qd, J = 18.0, 1.2 Hz, 2H), 2.67 (s, 2H), 2.41 (s, 2H), 2.35 (s, 1H), 2.16 (s, 3H), 1.16 (d, J = 5.4 Hz, 6H). |
| 79 | Light yellow solid | 180-182 | ¹H NMR (600 MHz, CDCl$_3$): δ 16.75 (s, 1H), 8.42 (s, 1H), 7.77 (d, J = 9.0 Hz, 1H), 7.40-7.33 (m, 5H), |

TABLE 1-continued

| NO. | Appearance | Melting point/° C. | ¹HNMR |
|---|---|---|---|
| | | | 7.33-7.27 (m, 3H), 7.24-7.19 (m, 2H), 5.51 (d, J = 16.8 Hz, 1H), 5.34 (d, J = 15.6 Hz, 1H), 2.76 (t, J = 6.0 Hz, 2H), 2.49 (t, J = 6.0 Hz, 2H), 2.21 (s, 3H), 2.07 (quintuplet, J = 6.6 Hz, 2H). |
| 80 | Pale brown solid | 146-148 | ¹H NMR (600 MHz, CDCl$_3$): δ 16.83 (s, 1H), 8.41 (d, J = 1.8 Hz, 1H), 7.75 (dd, J = 9.0, 1.8 Hz, 1H), 7.41-7.33 (m, 5H), 7.33-7.27 (m, 3H), 7.24-7.19 (m, 2H), 5.51 (d, J = 16.8 Hz, 1H), 5.34 (d, J = 15.6 Hz, 1H), 2.64 (s, 2H), 2.38 (s, 2H), 2.21 (s, 3H), 1.14 (d, J = 5.4 Hz, 6H). |
| 81 | Light yellow solid | 182-184 | ¹H NMR (600 MHz, CDCl$_3$): δ 16.83 (s, 1H), 8.41 (s, 1H), 7.75 (d, J = 8.4 Hz, 1H), 7.41-7.33 (m, 3H), 7.27 (d, J = 8.4 Hz, 1H), 7.23-7.19 (m, 2H), 6.87 (d, J = 7.8 Hz, 1H), 6.85-6.80 (m, 2H), 5.51 (d, J = 16.2 Hz, 1H), 5.27 (d, J = 15.6 Hz, 1H), 3.78 (s, 3H), 2.64 (s, 2H), 2.38 (s, 2H), 2.21 (s, 3H), 1.14 (d, J = 4.8 Hz, 6H). |
| 82 | White solid | 230-232 | ¹H NMR (600 MHz, CDCl$_3$): δ 17.65 (s, 1H), 7.40 (d, J = 9.0 Hz, 1H), 7.38-7.30 (m, 3H), 7.20 (d, J = 8.4 Hz, 1H), 7.14 (d, J = 6.6 Hz, 1H), 3.65 (s, 3H), 2.81 (t, J = 6.0 Hz, 2H), 2.67 (s, 3H), 2.46 (t, J = 6.0 Hz, 2H), 2.17 (s, 3H), 2.07 (quintuplet, J = 6.6 Hz, 2H). |
| 83 | Light brown solid | 178-180 | ¹H NMR (600 MHz, CDCl$_3$): δ 16.75 (s, 1H), 7.80 (d, J = 9.0 Hz, 1H), 7.41-7.33 (m, 3H), 7.29 (q, J = 6.6 Hz, 1H), 7.25-7.19 (m, 3H), 7.15-7.08 (m, 2H), 5.56 (d, J = 16.2 Hz, 1H), 5.41 (d, J = 16.8 Hz, 1H), 2.76 (t, J = 6.0 Hz, 2H), 2.50 (brs, 2H), 2.21 (s, 3H), 2.08 (quintuplet, J = 6.0 Hz, 2H). |
| 84 | Light yellow solid | 173-175 | ¹H NMR (600 MHz, CDCl$_3$): δ 16.76 (s, 1H), 8.42 (s, 1H), 7.77 (d, J = 8.4 Hz, 1H), 7.41-7.32 (m, 3H), 7.27 (d, J = 7.8 Hz, 1H), 7.24-7.19 (m, 2H), 6.88 (d, J = 7.8 Hz, 1H), 6.86-6.80 (m, 2H), 5.50 (d, J = 15.0 Hz, 1H), 5.27 (d, J = 15.6 Hz, 1H), 3.78 (s, 3H), 2.75 (t, J = 6.0 Hz, 2H), 2.49 (t, J = 6.0 Hz, 2H), 2.21 (s, 3H), 2.07 (quintuplet, J = 6.0 Hz, 2H). |
| 85 | Light brown solid | 176-178 | ¹H NMR (600 MHz, CDCl$_3$): δ 16.83 (s, 1H), 8.41 (s, 1H), 7.78 (d, J = 9.0 Hz, 1H), 7.41-7.33 (m, 3H), 7.29 (q, J = 7.2 Hz, 1H), 7.25-7.19 (m, 3H), 7.14-7.08 (m, 2H), 5.56 (d, J = 16.8 Hz, 1H), 5.42 (d, J = 16.2 Hz, 1H), 2.65 (s, 2H), 2.38 (s, 2H), 2.20 (s, 3H), 1.14 (d, J = 5.4 Hz, 6H). |
| 86 | Light yellow solid | 196-198 | ¹H NMR (600 MHz, CDCl$_3$): δ 16.82 (s, 1H), 8.41 (d, J = 1.2 Hz, 1H), 7.87 (d, J = 8.4 Hz, 1H), 7.63 (d, J = 8.4 Hz, 1H), 7.45 (t, J = 7.8 Hz, 1H), 7.42-7.34 (m, 2H), 7.20 (d, J = 7.8 Hz, 1H), 2.77 (t, J = 6.0 Hz, 2H), 2.55 (s, 3H), 2.52 (t, J = 6.0 Hz, 2H), 2.16 (s, 3H), 2.09 (quintuplet, J = 6.0 Hz, 2H). |
| 87 | White solid | 239-241 | ¹H NMR (600 MHz, CDCl$_3$): δ 16.89 (s, 1H), 8.40 (s, 1H), 7.85 (d, J = 8.4 Hz, 1H), 7.64 (d, J = 8.4 Hz, 1H), 7.45 (t, J = 7.8 Hz, 1H), 7.42-7.33 (m, 2H), 7.20 (d, J = 7.8 Hz, 1H), 2.66 (s, 2H), 2.55 (s, 3H), 2.41 (s, 2H), 2.16 (s, 3H), 1.16 (d, J = 1.8 Hz, 6H). |
| 88 | Light yellow solid | 161-163 | ¹H NMR (600 MHz, CDCl$_3$): δ 17.66 (s, 1H), 7.41 (t, J = 7.8 Hz, 1H), 7.38 (d, J = 8.4 Hz, 1H), 7.19 (d, J = 8.4 Hz, 2H), 7.06 (dd, J = 19.2, 7.8 Hz, 2H), 3.80 (s, 3H), 3.64 (s, 3H), 2.81 (t, J = 6.0 Hz, 2H), 2.68 (s, 2H), 2.45 (t, J = 6.0 Hz, 2H), 2.06 (quintuplet, J = 6.0 Hz, 2H). |
| 89 | White solid | 179-181 | ¹H NMR (600 MHz, CDCl$_3$): δ 16.88 (s, 1H), 8.42 (s, 1H), 7.88 (d, J = 7.8 Hz, 1H), 7.42 (s, 2H), 7.34 (s, 1H), 7.29 (d, J = 8.4 Hz, 1H), 7.13 (d, J = 6.6 Hz, 1H), 3.68 (s, 3H), 2.66 (s, 2H), 2.47 (q, J = 7.2 Hz, 2H), 2.40 (s, 2H), 1.21-1.12 (m, 9H). |
| 90 | Light yellow solid | 247-249 | ¹H NMR (600 MHz, CDCl$_3$): δ 16.78 (s, 1H), 8.39 (s, 1H), 7.89 (d, J = 9.0 Hz, 1H), 7.64 (d, J = 7.8 Hz, 2H), 7.28 (d, J = 9.6 Hz, 1H), 7.15 (d, J = 8.4 Hz, 2H), 3.66 (s, 3H), 2.82 (d, J = 18.6 Hz, 1H), 2.59 (d, J = 16.8 Hz, 1H), 2.49 (dd, J = 18.0, 10.8 Hz, 1H), 2.42-2.31 (m, 1H), 2.26-2.15 (m, 1H), 1.15 (d, J = 6.0 Hz, 6H). |
| 91 | Beige solid | 221-223 | ¹H NMR (600 MHz, CDCl$_3$): δ 17.64 (s, 1H), 7.83 (d, J = 7.2 Hz, 1H), 7.72 (t, J = 7.8 Hz, 1H), 7.60 (t, J = 7.8 Hz, 1H), 7.42 (d, J = 9.0 Hz, 1H), 7.35 (d, J = 7.8 Hz, 1H), 7.21 (d, J = 9.0 Hz, 1H), 3.64 (s, 3H), 2.68 (s, 2H), 2.64 (s, 3H), 2.33 (s, 2H), 1.13 (s, 6H). |
| 92 | White solid | 262-264 | ¹H NMR (600 MHz, CDCl$_3$): δ 17.64 (s, 1H), 7.83 (d, J = 7.2 Hz, 1H), 7.72 (t, J = 7.8 Hz, 1H), 7.60 (t, J = 7.2 Hz, 1H), 7.41 (d, J = 8.4 Hz, 1H), 7.35 (d, J = 7.8 Hz, 1H), 7.20 (d, J = 8.4 Hz, 1H), 3.64 (s, 3H), 2.81 (t, J = 6.0 Hz, 2H), 2.65 (s, 3H), 2.46 (t, J = 6.0 Hz, 2H), 2.07 (quintuplet, J = 6.0 Hz, 2H). |

TABLE 1-continued

| NO. | Appearance | Melting point/° C. | $^1$HNMR |
|---|---|---|---|
| 93 | White solid | 206-208 | $^1$H NMR (600 MHz, CDCl$_3$): δ 17.67 (s, 1H), 7.41 (d, J = 9.0 Hz, 1H), 7.25-7.16 (m, 5H), 3.66 (s, 3H), 2.82 (t, J = 6.0 Hz, 2H), 2.68 (s, 3H), 2.47 (t, J = 6.0 Hz, 2H), 2.13 (s, 7H), 2.07 (quintuplet, J = 6.6 Hz, 2H). |
| 94 | Beige solid | 228-230 | $^1$H NMR (600 MHz, CDCl$_3$): δ 16.92 (s, 1H), 8.44 (d, J = 2.4 Hz, 1H), 7.89 (dd, J = 9.0, 1.8 Hz, 1H), 7.49 (d, J = 7.8 Hz, 2H), 7.37 (t, J = 7.8 Hz, 1H), 7.31 (d, J = 8.4 Hz, 1H), 3.70 (s, 3H), 2.67 (s, 2H), 2.41 (s, 2H), 1.16 (s, 6H). |
| 95 | Light yellow solid | 188-190 | $^1$H NMR (600 MHz, CDCl$_3$): δ 16.82 (s, 1H), 8.45 (d, J = 1.2 Hz, 1H), 7.91 (dd, J = 8.4, 0.6 Hz, 1H), 7.39 (d, J = 7.8 Hz, 1H), 7.33-7.28 (m, 2H), 3.69 (s, 3H), 2.78 (t, J = 6.6 Hz, 2H), 2.52 (t, J = 6.0 Hz, 2H), 2.20 (s, 3H), 2.10 (quintuplet, J = 6.6 Hz, 2H). |
| 96 | White solid | 189-191 | $^1$H NMR (600 MHz, CDCl$_3$): δ 16.92 (s, 1H), 8.44 (d, J = 0.6 Hz, 1H), 7.89 (dd, J = 6.6, 0.6 Hz, 1H), 7.39 (d, J = 7.2 Hz, 1H), 7.33-7.28 (m, 2H), 3.70 (s, 3H), 2.67 (s, 2H), 2.42 (s, 2H), 2.20 (s, 3H), 1.17 (s, 6H). |
| 97 | White solid | 232-234 | $^1$H NMR (600 MHz, CDCl$_3$): δ 16.90 (s, 1H), 8.42 (d, J = 1.8 Hz, 1H), 7.87 (dd, J = 9.0, 1.8 Hz, 1H), 7.46 (q, J = 8.4 Hz, 2H), 7.32 (td, J = 7.8, 1.8 Hz, 1H), 7.29 (d, J = 8.4 Hz, 1H), 7.10 (d, J = 7.8 Hz, 1H), 3.68 (s, 3H), 2.72 (dt, J = 13.8, 7.2 Hz, 1H), 2.66 (s, 2H), 2.48-2.34 (m, 2H), 1.24-1.11 (m, 12H). |
| 98 | White solid | 181-183 | $^1$H NMR (600 MHz, CDCl$_3$): δ 16.91 (s, 1H), 8.44 (d, J = 1.2 Hz, 1H), 7.88 (dd, J = 9.0, 1.8 Hz, 1H), 7.30 (d, J = 9.0 Hz, 1H), 7.24 (d, J = 7.2 Hz, 1H), 7.18 (d, J = 7.8 Hz, 2H), 3.69 (s, 3H), 2.67 (s, 2H), 2.41 (s, 2H), 2.12 (s, 6H), 1.16 (s, 6H). |

Test Example 1

This test example is for describing the herbicidal activity inhibition ratio (%) (the dose is 150 g/ha) of the compound with a structure shown in Formula (I).

Primary screening test (pot culture method): The test targets are *abutilon theophrasti, digitaria sanguinalis, amaranthus retroflexus, echinochloa crusgalli, eclipta prostrata* and *setaria viridis*. Take flowerpots with an inner diameter of 6 cm, put composite soil (vegetable garden soil:seedling matrix=1:2, v/v) into them till ¾ of flowerpot height, directly sow the above six weed targets (budding rate>85%), cover them with 0.2 cm thick soil, and keep them for future use when the weeds grow to 3-leaf stage. Each compound is dissolved in N,N-dimethylformamide at a dose of 150 g/ha and diluted with distilled water into a 0.2 g/L solution. The solution is sprayed through an automatic spray tower. After the solution on weed leaves is aired dry, the flowerpots are moved into a greenhouse for cultivation. The result is investigated 15 days later. Its inhibition ratio (%) is shown in Table 2.

TABLE 2

| NO. | *Abutilon theophrasti* | *Digitaria sanguinalis* | *Amaranthus retroflexus* | *Echinochloa crusgalli* | *Eclipta prostrata* | *Setaria viridis* |
|---|---|---|---|---|---|---|
| 1 | 90 | 90 | 90 | 90 | 85 | 100 |
| 2 | 100 | 90 | 95 | 80 | 75 | 80 |
| 3 | 80 | 70 | 100 | 80 | 80 | 100 |
| 4 | 100 | 100 | 100 | 85 | 90 | 90 |
| 5 | 85 | 100 | 80 | 80 | 80 | 100 |
| 6 | 100 | 75 | 80 | 80 | 85 | 90 |
| 7 | 100 | 70 | 90 | 80 | 60 | 80 |
| 8 | 0 | 90 | 100 | 75 | 80 | 85 |
| 9 | 100 | 75 | 100 | 85 | 95 | 100 |
| 10 | 100 | 75 | 85 | 85 | 80 | 80 |
| 11 | 85 | 95 | 85 | 85 | 85 | 80 |
| 12 | 85 | 80 | 80 | 80 | 80 | 100 |
| 13 | 100 | 90 | 100 | 90 | 90 | 100 |
| 14 | 75 | 75 | 100 | 75 | 75 | 75 |
| 15 | 60 | 75 | 70 | 70 | 60 | 75 |
| 16 | 70 | 100 | 70 | 85 | 75 | 100 |
| 17 | 70 | 75 | 100 | 70 | 95 | 100 |
| 18 | 75 | 90 | 100 | 70 | 75 | 85 |
| 19 | 75 | 85 | 100 | 70 | 85 | 100 |
| 20 | 100 | 100 | 100 | 100 | 95 | 100 |
| 21 | 85 | 85 | 100 | 85 | 95 | 100 |
| 22 | 100 | 95 | 100 | 80 | 90 | 95 |
| 23 | 85 | 30 | 95 | 85 | 50 | 45 |
| 24 | 93 | 60 | 80 | 30 | 83 | 10 |
| 25 | 80 | 80 | 95 | 80 | 83 | 35 |
| 26 | 100 | 93 | 100 | 85 | 88 | 30 |
| 27 | 83 | 90 | 100 | 90 | 80 | 60 |

TABLE 2-continued

| NO. | Abutilon theophrasti | Digitaria sanguinalis | Amaranthus retroflexus | Echinochloa crusgalli | Eclipta prostrata | Setaria viridis |
|---|---|---|---|---|---|---|
| 28 | 100 | 95 | 95 | 85 | 83 | 35 |
| 29 | 90 | 88 | 100 | 90 | 65 | 60 |
| 30 | 100 | 60 | 100 | 85 | 60 | 30 |
| 31 | 60 | 60 | 80 | 40 | 55 | 10 |
| 32 | 80 | 80 | 85 | 80 | 50 | 40 |
| 33 | 85 | 80 | 90 | 85 | 83 | 60 |
| 34 | 90 | 83 | 100 | 90 | 80 | 80 |
| 35 | 80 | 65 | 100 | 65 | 70 | 50 |
| 36 | 50 | 100 | 35 | 25 | 0 | 50 |
| 37 | 65 | 83 | 95 | 80 | 80 | 40 |
| 38 | 90 | 85 | 100 | 90 | 75 | 80 |
| 39 | 95 | 85 | 98 | 70 | 85 | 80 |
| 40 | 100 | 85 | 95 | 78 | 80 | 45 |
| 41 | 100 | 85 | 95 | 73 | 80 | 25 |
| 42 | 98 | 93 | 100 | 88 | 83 | 60 |
| 43 | 65 | 60 | 98 | 80 | 83 | 50 |
| 44 | 85 | 75 | 100 | 65 | 0 | 60 |
| 45 | 60 | 40 | 90 | 50 | 83 | 10 |
| 46 | 35 | 55 | 100 | 60 | 70 | 20 |
| 47 | 100 | 95 | 100 | 85 | 85 | 83 |
| 48 | 50 | 85 | 95 | 85 | 85 | 50 |
| 49 | 100 | 90 | 95 | 65 | 80 | 50 |
| 50 | 50 | 60 | 95 | 78 | 80 | 50 |
| 51 | 93 | 83 | 90 | 50 | 80 | 40 |
| 52 | 55 | 50 | 98 | 85 | 75 | 80 |
| 53 | 100 | 25 | 80 | 0 | 80 | 80 |
| 54 | 100 | 60 | 98 | 95 | 80 | 45 |
| 55 | 100 | 60 | 95 | 93 | 68 | 25 |
| 56 | 55 | 55 | 80 | 60 | 75 | 60 |
| 57 | 60 | 75 | 95 | 85 | 80 | 50 |
| 58 | 100 | 88 | 90 | 80 | 68 | 60 |
| 59 | 0 | 0 | 30 | 0 | 25 | 10 |
| 60 | 100 | 40 | 70 | 65 | 0 | 80 |
| 61 | 65 | 25 | 0 | 0 | 20 | 10 |
| 62 | 100 | 65 | 88 | 83 | 20 | 93 |
| 63 | 100 | 20 | 30 | 25 | 50 | 30 |
| 64 | 95 | 60 | 80 | 90 | 0 | 93 |
| 65 | 98 | 100 | 90 | 80 | 80 | 98 |
| 66 | 100 | 95 | 93 | 100 | 95 | 100 |
| 67 | 95 | 80 | 80 | 83 | 0 | 80 |
| 68 | 15 | 0 | 0 | 0 | 0 | 10 |
| 69 | 100 | 30 | 95 | 90 | 88 | 85 |
| 70 | 100 | 90 | 98 | 100 | 100 | 100 |
| 71 | 95 | 25 | 85 | 80 | 98 | 98 |
| 72 | 100 | 20 | 20 | 30 | 60 | 30 |
| 73 | 50 | 0 | 30 | 0 | 0 | 10 |
| 74 | 50 | 0 | 0 | 0 | 0 | 10 |
| 75 | 90 | 0 | 20 | 0 | 20 | 10 |
| 76 | 20 | 0 | 0 | 0 | 0 | 10 |
| 77 | 90 | 0 | 90 | 50 | 35 | 20 |
| 78 | 0 | 0 | 0 | 0 | 0 | 10 |
| 79 | 0 | 0 | 0 | 0 | 0 | 10 |
| 80 | 0 | 0 | 0 | 0 | 0 | 10 |
| 81 | 0 | 0 | 0 | 0 | 0 | 10 |
| 82 | 100 | 100 | 100 | 100 | 100 | 100 |
| 83 | 0 | 30 | 0 | 50 | 90 | 50 |
| 84 | 0 | 25 | 0 | 50 | 80 | 10 |
| 85 | 0 | 0 | 20 | 20 | 0 | 10 |
| 86 | 20 | 30 | 0 | 85 | 30 | 10 |
| 87 | 0 | 0 | 0 | 25 | 0 | 10 |
| 88 | 100 | 100 | 100 | 100 | 100 | 100 |
| 89 | 100 | 60 | 100 | 80 | 70 | 75 |
| 90 | 92.5 | 93 | 20 | 90 | 83 | 85 |
| 91 | 100 | 100 | 100 | 100 | 100 | 100 |
| 92 | 100 | 100 | 100 | 100 | 100 | 100 |
| 93 | 100 | 100 | 100 | 100 | 100 | 100 |
| 94 | 95 | 88 | 95 | 93 | 98 | 95 |
| 95 | 100 | 90 | 100 | 100 | 70 | 100 |
| 96 | 95 | 30 | 100 | 55 | 83 | 95 |
| 97 | 98 | 50 | 100 | 55 | 90 | 50 |
| 98 | 100 | 50 | 100 | 85 | 88 | 80 |

Secondary Screening Test:

By the same method adopted in primary screening test, a secondary screening test is done on some typical compounds, such as: 5, 6, 20, 21, 23, 34, 47, 65, 66, 70 and 91 at a reduced dose, and the test result is compared with mesotrione which is commercially available and has a good herbicidal effect. The test method is same as that adopted in primary screening test. The test result of inhibition ratio % is shown in Table 3. Mesotrione is bought from Hubei Litian Chemical Co., Ltd.

TABLE 3

| NO. | Dose (g/ha) | Echinochloa crusgalli | Digitaria sanguinalis | Setaria viridis | Abutilon theophrasti | Amaranthus retroflexus | Eclipta prostrata |
|---|---|---|---|---|---|---|---|
| 5 | 37.5 | 60 | 40 | 60 | 60 | 60 | 30 |
|  | 75 | 90 | 90 | 90 | 70 | 75 | 40 |
| 6 | 37.5 | 70 | 60 | 60 | 70 | 70 | 70 |
|  | 75 | 75 | 70 | 60 | 70 | 75 | 70 |
| 20 | 37.5 | 50 | 40 | 50 | 30 | 50 | 50 |
|  | 75 | 60 | 70 | 70 | 85 | 60 | 50 |
| 21 | 37.5 | 70 | 70 | 70 | 70 | 80 | 40 |
|  | 75 | 75 | 75 | 75 | 100 | 90 | 50 |
| 23 | 37.5 | 20 | 20 | 30 | 100 | 100 | 100 |
|  | 75 | 20 | 65 | 50 | 100 | 100 | 100 |
| 34 | 37.5 | 65 | 55 | 70 | 30 | 100 | 30 |
|  | 75 | 80 | 75 | 78 | 50 | 100 | 50 |
| 47 | 37.5 | 80 | 80 | 88 | 60 | 90 | 20 |
|  | 75 | 88 | 85 | 90 | 90 | 95 | 30 |
| 65 | 37.5 | 95 | 30 | 80 | 50 | 50 | 30 |
|  | 75 | 100 | 40 | 85 | 70 | 60 | 50 |
| 66 | 37.5 | 100 | 60 | 97.5 | 100 | 90 | 95 |
|  | 75 | 100 | 97.5 | 100 | 100 | 100 | 100 |
| 70 | 37.5 | 40 | 80 | 83 | 50 | 50 | 60 |
|  | 75 | 55 | 75 | 93 | 73 | 70 | 78 |
| 91 | 37.5 | 65 | 70 | 100 | 85 | 60 | 80 |
|  | 75 | 90 | 90 | 100 | 93 | 80 | 93 |
| Mesotrione | 37.5 | 50 | 40 | 0 | 100 | 70 | 75 |
|  | 75 | 70 | 70 | 0 | 100 | 75 | 85 |

The result shown in Table 3 indicates the above compounds have higher activity than control agent mesotrione in killing *echinochloa crusgalli, digitaria sanguinalis, setaria viridis, abutilon theophrasti* and *amaranthus retroflexus* and moreover they can also prevent and control gramineae weeds, such as: *setaria viridis*, which cannot be prevented and controlled by mesotrione.

Test Example 2

This test example is for describing crop safety of the compound with a structure shown in Formula (1).

Crop safety test method (pot culture method): The test targets are wheat and maize. Take flowerpots with an inner diameter of 12 cm, put composite soil (vegetable garden soil:seedling matrix=1:2, v/v) into them till ¾ of flowerpot height, directly sow the crop seeds (budding rate>85%), cover them with 0.2 cm thick soil, and keep the plants for future use when they grow to have about 4-5 leaves. Each compound is dissolved in N,N-dimethylformamide at doses of 75 g/ha or 150 g/ha and diluted with distilled water containing 0.1% tween-80 emulsifier to form 0.1 g/L (75 g/ha) solution and 0.2 g/L (150 g/ha) solution respectively. The solutions are sprayed through an automatic spray tower. After the solutions on weed leaves are dried in the air, the flowerpots are moved into a greenhouse for cultivation. The result is investigated 15 days later. Its inhibition ratio (%) is shown in Table 4.

TABLE 4

| NO. | Dose (g/ha) | Maize | Wheat |
|---|---|---|---|
| 5 | 75 | 0 | 0 |
|  | 150 | 15 | 0 |
| 6 | 75 | 0 | 0 |
|  | 150 | 15 | 0 |
| 20 | 75 | 0 | 0 |
|  | 150 | 15 | 0 |

TABLE 4-continued

| NO. | Dose (g/ha) | Maize | Wheat |
|---|---|---|---|
| 21 | 75 | 0 | 0 |
|  | 150 | 15 | 0 |
| 23 | 75 | 0 | 0 |
|  | 150 | 0 | 5 |
| 34 | 75 | 0 | 0 |
|  | 150 | 0 | 5 |
| 47 | 75 | 0 | 0 |
|  | 150 | 0 | 0 |
| 65 | 75 | 0 | 0 |
|  | 150 | 10 | 10 |
| 66 | 75 | 0 | 0 |
|  | 150 | 5 | 10 |
| 70 | 75 | 0 | 0 |
|  | 150 | 15 | 10 |
| 91 | 75 | 0 | 0 |
|  | 150 | 10 | 10 |
| Mesotrione | 75 | 7 | 10 |
|  | 150 | 15 | 40 |

The result shown in Table 4 indicates the above compounds may be used as herbicides in wheat fields and all the compounds at a dose of 75 g/ha may be used as herbicides in maize fields. Particularly, compounds 23, 34 and 47 at a dose of 150 g/ha are highly safe to maize fields. Further, at the same dose, the compounds are safer than herbicide mesotrione sold in the market.

To summarize, the triketone compound described in the present invention and containing a quinazolinedione structure has an effect in preventing and controlling weeds, particularly broadleaved weeds and/or gramineae weeds, and their safety is universally high.

The preferred embodiments of the present invention are described in details above, but the present invention is not limited to the concrete details of the foregoing embodiments. Within the scope of technical conception of the present invention, the technical solutions of the present invention may be modified in simple and multiple ways. These simple modifications are all within the scope of protection of the present invention.

Further, it should be noted that the concrete technical features described in the foregoing embodiments may be combined in any appropriate manner, provided that no conflict occurs. In order to avoid unnecessary repetition, the present invention does not describe all the possible combinations.

Further, the embodiments of the present invention may be freely combined, provided that the combinations do not go against the intention of the present invention. Likewise, the combinations shall also be deemed as contents disclosed by the present invention.

The invention claimed is:

1. A triketone compound having a structure shown in Formula (I):

Formula (I)

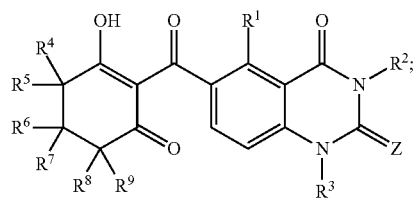

wherein,

Z is O or S;

$R^1$ is one of H, $C_1$-$C_6$ alkyl, halogen, nitro, $C_1$-$C_6$ alkoxy and cyano;

$R^2$ is one of substituted or unsubstituted phenyl, benzyl, diaromatic groups and triaromatic groups;

$R^3$ is one of H, $C_1$-$C_6$ alkyl, $C_2$-$C_6$ unsaturated chain alkyl, substituted or unsubstituted phenyl, and substituted or unsubstituted benzyl;

$R^4$, $R^5$, $R^6$, $R^7$, $R^8$ and $R^9$ are respectively one of H, $C_1$-$C_6$ alkyl, $C_1$-$C_6$ alkoxy and halogen.

2. The triketone compound according to claim 1, wherein,

Z is O;

$R^1$ is one of H and $C_1$-$C_3$ alkyl;

$R^2$ is one of substituted or unsubstituted phenyl and substituted or unsubstituted diaromatic groups;

$R^3$ is one of H, $C_1$-$C_6$ alkyl, $C_2$-$C_4$ unsaturated chain alkyl, substituted or unsubstituted phenyl, and substituted or unsubstituted benzyl;

$R^4$, $R^5$, $R^6$, $R^7$, $R^8$ and $R^9$ are respectively one of H, $C_1$-$C_6$ alkyl.

3. The triketone compound according to claim 1, wherein, $R^1$ is H or methyl;

$R^4$, $R^5$, $R^6$, $R^7$, $R^8$ and $R^9$ are respectively H or methyl.

4. The triketone compound according to claim 1, wherein the triketone compound is one selected from a compound shown in Table A and Table B:

TABLE A

| NO. | $R^1$ | $R^2$ | $R^3$ | $R^4$ | $R^5$ | $R^6$ | $R^7$ | $R^8$ | $R^9$ | Z |
|---|---|---|---|---|---|---|---|---|---|---|
| 1 | H | 4-Cl—$C_6H_4$ | $CH_3$ | H | H | H | H | H | H | O |
| 2 | H | 4-Cl—$C_6H_4$ | $CH_3$ | H | H | $CH_3$ | $CH_3$ | H | H | O |
| 3 | H | 3-Cl—$C_6H_4$ | $CH_3$ | H | H | H | H | H | H | O |
| 4 | H | 3-Cl—$C_6H_4$ | $CH_3$ | H | H | $CH_3$ | $CH_3$ | H | H | O |
| 5 | H | 2-Cl—$C_6H_4$ | $CH_3$ | H | H | H | H | H | H | O |
| 6 | H | 2-Cl—$C_6H_4$ | $CH_3$ | H | H | $CH_3$ | $CH_3$ | H | H | O |
| 7 | H | 3,5-di-Cl—$C_6H_3$ | $CH_3$ | H | H | H | H | H | H | O |
| 8 | H | 3,5-di-Cl—$C_6H_3$ | $CH_3$ | H | H | $CH_3$ | $CH_3$ | H | H | O |
| 9 | H | 4-F—$C_6H_4$ | $CH_3$ | H | H | H | H | H | H | O |
| 10 | H | 3-F—$C_6H_4$ | $CH_3$ | H | H | H | H | H | H | O |
| 11 | H | 3-F—$C_6H_4$ | $CH_3$ | H | H | $CH_3$ | $CH_3$ | H | H | O |
| 12 | H | 2-F—$C_6H_4$ | $CH_3$ | H | H | H | H | H | H | O |
| 13 | H | 2-F—$C_6H_4$ | $CH_3$ | H | H | $CH_3$ | $CH_3$ | H | H | O |
| 14 | H | 4-$CH_3$—$C_6H_4$ | $CH_3$ | H | H | H | H | H | H | O |
| 15 | H | 4-$CH_3$—$C_6H_4$ | $CH_3$ | H | H | $CH_3$ | $CH_3$ | H | H | O |
| 16 | H | 4-$CH_3$—$C_6H_4$ | $CH_3$ | H | H | H | $CH_3$ | H | H | O |
| 17 | H | 3-$CH_3$—$C_6H_4$ | $CH_3$ | H | H | H | H | H | H | O |
| 18 | H | 3-$CH_3$—$C_6H_4$ | $CH_3$ | H | H | $CH_3$ | $CH_3$ | H | H | O |
| 19 | H | 3-$CH_3$—$C_6H_4$ | $CH_3$ | H | H | $CH_3$ | H | H | H | O |
| 20 | H | 2-$CH_3$—$C_6H_4$ | $CH_3$ | H | H | H | H | H | H | O |
| 21 | H | 2-$CH_3$—$C_6H_4$ | $CH_3$ | H | H | $CH_3$ | $CH_3$ | H | H | O |
| 22 | H | 4-F—$C_6H_4$ | $CH_3$ | H | H | $CH_3$ | $CH_3$ | H | H | O |
| 23 | H | 3-Br—$C_6H_4$ | $CH_3$ | H | H | H | H | H | H | O |
| 24 | H | 3-Br—$C_6H_4$ | $CH_3$ | H | H | $CH_3$ | $CH_3$ | H | H | O |
| 25 | H | 4-Br—$C_6H_4$ | $CH_3$ | H | H | H | H | H | H | O |
| 26 | H | 4-Br—$C_6H_4$ | $CH_3$ | H | H | $CH_3$ | $CH_3$ | H | H | O |
| 27 | H | 2-Br—$C_6H_4$ | $CH_3$ | H | H | H | H | H | H | O |
| 28 | H | 2-Br—$C_6H_4$ | $CH_3$ | H | H | $CH_3$ | $CH_3$ | H | H | O |
| 29 | H | 2-$OCH_3$—$C_6H_4$ | $CH_3$ | H | H | H | H | H | H | O |
| 30 | H | 4-$CF_3$—$C_6H_4$ | $CH_3$ | H | H | H | H | H | H | O |
| 31 | H | 4-$CF_3$—$C_6H_4$ | $CH_3$ | H | H | $CH_3$ | $CH_3$ | H | H | O |
| 32 | H | 2,6-di-Cl—$C_6H_3$ | $CH_3$ | H | H | H | H | H | H | O |
| 33 | H | 2-$CH_3$-5-Cl—$C_6H_3$ | $CH_3$ | H | H | H | H | H | H | O |
| 34 | H | 2,6-di-$CH_3$—$C_6H_3$ | $CH_3$ | H | H | H | H | H | H | O |
| 35 | H | $C_6H_5$ | $CH_3$ | H | H | H | H | H | H | O |

TABLE A-continued

| NO. | R¹ | R² | R³ | R⁴ | R⁵ | R⁶ | R⁷ | R⁸ | R⁹ | Z |
|---|---|---|---|---|---|---|---|---|---|---|
| 36 | H | 4-CH(CH₃)₂—C₆H₄ | CH₃ | H | H | H | H | H | H | O |
| 37 | H | 2-CH₃-5-Cl—C₆H₃ | CH₃ | H | H | CH₃ | CH₃ | H | H | O |
| 38 | H | 2-CF₃—C₆H₄ | CH₃ | H | H | H | H | H | H | O |
| 39 | H | 2-OCF₃—C₆H₄ | CH₃ | H | H | H | H | H | H | O |
| 40 | H | C₆H₅ | CH₃ | H | H | CH₃ | CH₃ | H | H | O |
| 41 | H | 2-CF₃—C₆H₄ | CH₃ | H | H | CH₃ | CH₃ | H | H | O |
| 42 | H | C₆H₅ | CH₃ | H | H | CH₃ | H | H | H | O |
| 43 | H | 4-Cl—C₆H₄ | CH₂CH₃ | H | H | H | H | H | H | O |
| 44 | H | 1-naphthyl | CH₃ | H | H | H | H | H | H | O |
| 45 | H | 4-NO₂—C₆H₄ | CH₃ | H | H | H | H | H | H | O |
| 46 | H | 2,6-di-CH(CH₃)₂—C₆H₃ | CH₃ | H | H | H | H | H | H | O |
| 47 | H | 2-CH₂CH₃—C₆H₄ | CH₃ | H | H | H | H | H | H | O |
| 48 | H | 2-OCH₃—C₆H₄ | CH₃ | H | H | CH₃ | CH₃ | H | H | O |
| 49 | H | 4-OCF₃—C₆H₄ | CH₃ | H | H | CH₃ | CH₃ | H | H | O |
| 50 | H | 4-OCF₃—C₆H₄ | CH₃ | H | H | H | H | H | H | O |
| 51 | H | 3-CF₃—C₆H₄ | CH₃ | H | H | CH₃ | CH₃ | H | H | O |
| 52 | H | 3-CF₃—C₆H₄ | CH₃ | H | H | H | H | H | H | O |
| 53 | H | 4-NO₂—C₆H₄ | CH₃ | H | H | CH₃ | CH₃ | H | H | O |
| 54 | H | 2,6-di-CH₃—C₆H₃ | CH₃ | CH₃ | CH₃ | H | H | H | H | O |
| 55 | H | 3-OCH₃—C₆H₄ | CH₃ | H | H | H | H | H | H | O |
| 56 | H | 3-OCH₃—C₆H₄ | CH₃ | H | H | CH₃ | CH₃ | H | H | O |
| 57 | H | 4-OCH₃—C₆H₄ | CH₃ | H | H | H | H | H | H | O |
| 58 | H | 4-OCH₃—C₆H₄ | CH₃ | H | H | CH₃ | CH₃ | H | H | O |
| 59 | H | 2-CH₃—C₆H₄ | H | H | H | CH₃ | CH₃ | H | H | O |
| 60 | H | 2-Cl-5-CF₃—C₆H₃ | CH₃ | H | H | H | H | H | H | O |
| 61 | H | 2-Cl-5-CF₃—C₆H₃ | CH₃ | H | H | CH₃ | CH₃ | H | H | O |
| 62 | H | 2,4-di-Cl—C₆H₃ | CH₃ | H | H | H | H | H | H | O |
| 63 | H | 2,4-di-Cl—C₆H₃ | CH₃ | H | H | CH₃ | CH₃ | H | H | O |
| 64 | H | 2,4-di-Cl—C₆H₃ | CH₃ | H | H | H | CH₃ | H | H | O |
| 65 | H | 2-CH(CH₃)₂—C₆H₄ | CH₃ | H | H | H | H | H | H | O |
| 66 | H | 2-CH₃—C₆H₄ | CH₂CH₃ | H | H | H | H | H | H | O |
| 67 | H | 2,4,6-tri-CH₃—C₆H₂ | CH₃ | H | H | H | H | H | H | O |
| 68 | H | 2-CH₃—C₆H₄ | H | H | H | H | H | H | H | O |
| 69 | H | 2-CH₃—C₆H₄ | CH₂CH₃ | H | H | CH₃ | CH₃ | H | H | O |
| 70 | H | 2-CH₃—C₆H₄ | CH₂CH₃ | H | H | H | CH₃ | H | H | O |

TABLE B

| NO. | R¹ | R² | R³ | R⁴ | R⁵ | R⁶ | R⁷ | R⁸ | R⁹ | Z |
|---|---|---|---|---|---|---|---|---|---|---|
| 71 | H | 2-CH₃—C₆H₄ | CH₂CH₂CH₃ | H | H | H | H | H | H | O |
| 72 | H | 2-CH₃—C₆H₄ | CH₂CH₂CH₃ | H | H | CH₃ | CH₃ | H | H | O |
| 73 | H | 2-CH₃—C₆H₄ | CH₂CH₂CH₂CH₃ | H | H | H | H | H | H | O |
| 74 | H | 2-CH₃—C₆H₄ | CH₂CH₂CH₂CH₃ | H | H | CH₃ | CH₃ | H | H | O |
| 75 | H | 2-CH₃—C₆H₄ | CH₂CH(CH₃)₂ | H | H | H | H | H | H | O |
| 76 | H | 2-CH₃—C₆H₄ | CH₂CH(CH₃)₂ | H | H | CH₃ | CH₃ | H | H | O |
| 77 | H | 2-CH₃—C₆H₄ | CH₂C≡CH | H | H | H | H | H | H | O |
| 78 | H | 2-CH₃—C₆H₄ | CH₂C≡CH | H | H | CH₃ | CH₃ | H | H | O |
| 79 | H | 2-CH₃—C₆H₄ | CH₂C₆H₅ | H | H | H | H | H | H | O |
| 80 | H | 2-CH₃—C₆H₄ | CH₂C₆H₅ | H | H | CH₃ | CH₃ | H | H | O |
| 81 | H | 2-CH₃—C₆H₄ | CH₂-3-OCH₃—C₆H₄ | H | H | CH₃ | CH₃ | H | H | O |
| 82 | CH₃ | 2-CH₃—C₆H₄ | CH₃ | H | H | H | H | H | H | O |
| 83 | H | 2-CH₃—C₆H₄ | CH₂-2-F—C₆H₄ | H | H | H | H | H | H | O |
| 84 | H | 2-CH₃—C₆H₄ | CH₂-3-OCH₃—C₆H₄ | H | H | H | H | H | H | O |
| 85 | H | 2-CH₃—C₆H₄ | CH₂-2-F—C₆H₄ | H | H | CH₃ | CH₃ | H | H | O |
| 86 | H | 2-CH₃—C₆H₄ | CH₃ | H | H | H | H | H | H | S |
| 87 | H | 2-CH₃—C₆H₄ | CH₃ | H | H | CH₃ | CH₃ | H | H | S |
| 88 | CH₃ | 2-OCH₃—C₆H₄ | CH₃ | H | H | H | H | H | H | O |
| 89 | H | 2-CH₂CH₃—C₆H₄ | CH₃ | H | H | CH₃ | CH₃ | H | H | O |
| 90 | H | 4-Br—C₆H₄ | CH₃ | H | H | CH₃ | H | H | H | O |
| 91 | CH₃ | 2-CF₃—C₆H₄ | CH₃ | H | H | CH₃ | CH₃ | H | H | O |
| 92 | CH₃ | 2-CF₃—C₆H₄ | CH₃ | H | H | H | H | H | H | O |
| 93 | CH₃ | 2,6-di-CH₃—C₆H₃ | CH₃ | H | H | H | H | H | H | O |
| 94 | H | 2,6-di-Cl—C₆H₃ | CH₃ | H | H | CH₃ | CH₃ | H | H | O |
| 95 | H | 2-CH₃-6-Cl—C₆H₃ | CH₃ | H | H | H | H | H | H | O |
| 96 | H | 2-CH₃-6-Cl—C₆H₃ | CH₃ | H | H | CH₃ | CH₃ | H | H | O |
| 97 | H | 2-CH(CH₃)₂C₆H₄ | CH₃ | H | H | H | H | H | H | O |
| 98 | H | 2,6-di-CH₃—C₆H₃ | CH₃ | H | H | CH₃ | CH₃ | H | H | O. |

5. A method for preparing the triketone compound with a structure shown in Formula (I), comprising the step of contacting the compound with a structure shown in Formula (II) with catalyst under the conditions of rearrangement reaction in the presence of alkali and solvent;

Formula (I)

[Chemical structure of Formula (I): a cyclohexenone ring bearing OH, $R^4$, $R^5$, $R^6$, $R^7$, $R^8$, $R^9$ substituents, connected through a C=O linker to a quinazolinedione-type bicyclic system with substituents $R^1$, $R^2$, $R^3$ and Z]

Formula (II)

[Chemical structure of Formula (II): a cyclohexenone ring bearing $R^4$, $R^5$, $R^6$, $R^7$, $R^8$, $R^9$ substituents, connected through an ester (–O–C(=O)–) linkage to the quinazolinedione-type bicyclic system with substituents $R^1$, $R^2$, $R^3$ and Z]

wherein,

Z is O or S;

$R^1$ is one of H, $C_1$-$C_6$ alkyl, halogen, nitro, $C_1$-$C_6$ alkoxy and cyano;

$R^2$ is one of substituted or unsubstituted phenyl, benzyl, diaromatic groups and triaromatic groups;

$R^3$ is one of H, $C_1$-$C_6$ alkyl, $C_2$-$C_6$ unsaturated chain alkyl, substituted or unsubstituted phenyl, and substituted or unsubstituted benzyl;

$R^4$, $R^5$, $R^6$, $R^7$, $R^8$ and $R^9$ are respectively one of H, $C_1$-$C_6$ alkyl, $C_1$-$C_6$ alkoxy and halogen.

6. The method according to claim 5, wherein the molar ratio of the compound with a structure shown in Formula (II) to catalyst and alkali is 1:0.01-1:0.5-4; the contact conditions are: reaction temperature being 0-100° C.; reaction time being 0.5-24 h.

7. The method according to claim 5, wherein the catalyst is at least one of sodium cyanide, potassium cyanide, acetone cyanohydrins, trimethyl silyl cyanide, 1,2,4-triazole and benzo-1,2,4-triazole;
the alkali is at least one of potassium carbonate, sodium carbonate, cesium carbonate, triethylamine and pyridine;
the solvent is at least one of dichloromethane, trichloromethane, dichloroethane, acetonitrile, toluene, tetrahydrofuran and benzene.

8. The method according to claim 6, wherein the catalyst is at least one of sodium cyanide, potassium cyanide, acetone cyanohydrins, trimethyl silyl cyanide, 1,2,4-triazole and benzo-1,2,4-triazole; the alkali is at least one of potassium carbonate, sodium carbonate, cesium carbonate, triethylamine and pyridine; the solvent is at least one of dichloromethane, trichloromethane, clichloroethane, acetonitrile, toluene, tetrahydrofuran and benzene.

9. A method of controlling weeds comprising applying the triketone compound of claim 1 to the weeds.

10. The method according to claim 9, wherein the weeds are broadleaved weeds and/or gramineae weeds.

11. The method according to claim 9, wherein the dose of the triketone compound is 50-300 g/ha.

12. The method according to claim 10, wherein the weeds are one or more of *abutilon theophrasti, digitaria sanguinalis, amaranthus retroflexus, echinochloa crusgalli, eclipta prostrata* and *setaria viridis*.

13. The method according to claim 12, wherein the dose of the triketone compound is 50-300 g/ha.

14. A method of controlling weeds comprising applying the triketone compound of claim 2 to the weeds.

15. The method according to claim 14, wherein the weeds are broadleaved weeds and/or gramineae weeds.

16. The method according to claim 15, wherein the weeds are one or more of *abutilon theophrasti, digitaria sanguinalis, amaranthus retroflexus, echinochloa crusgalli, eclipta prostrata* and *setaria viridis*.

17. The method according to claim 15, wherein the dose of the triketone compound is 50-300 g/ha.

18. The method according to claim 16, wherein the dose of the triketone compound is 50-300 g/ha.

19. A method of controlling weeds comprising applying the triketone compound of claim 3 to the weeds.

20. A method of controlling weeds comprising applying the triketone compound of claim 4 to the weeds.

* * * * *